(12) United States Patent
Simon et al.

(10) Patent No.: US 9,567,391 B2
(45) Date of Patent: Feb. 14, 2017

(54) JCV NEUTRALIZING ANTIBODIES

(71) Applicant: Biogen Idec MA Inc., Cambridge, MA (US)

(72) Inventors: Kenneth Simon, Cambridge, MA (US); Thomas Cameron, Cambridge, MA (US); Mia Rushe, Everett, MA (US); Justin Caravella, Cambridge, MA (US); George Campbell Kaynor, Melrose, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 14/386,228

(22) PCT Filed: Mar. 15, 2013

(86) PCT No.: PCT/US2013/031853
§ 371 (c)(1),
(2) Date: Sep. 18, 2014

(87) PCT Pub. No.: WO2013/142300
PCT Pub. Date: Sep. 26, 2013

(65) Prior Publication Data
US 2015/0056188 A1  Feb. 26, 2015

Related U.S. Application Data

(60) Provisional application No. 61/613,249, filed on Mar. 20, 2012.

(51) Int. Cl.
*A61K 39/395* (2006.01)
*C07K 16/08* (2006.01)
*A61K 39/00* (2006.01)

(52) U.S. Cl.
CPC ....... *C07K 16/084* (2013.01); *A61K 2039/505* (2013.01); *C07K 2317/00* (2013.01); *C07K 2317/24* (2013.01); *C07K 2317/40* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 2007/0280941 A1 | 12/2007 | Chung et al. |
| 2009/0148447 A1 | 6/2009 | Ledbetter et al. |
| 2009/0280128 A1 | 11/2009 | Kamogawa et al. |
| 2010/0028336 A1 | 2/2010 | Ebel et al. |
| 2010/0129437 A1 | 5/2010 | Gaillard |
| 2011/0219478 A1 | 9/2011 | Kav et al. |
| 2015/0050271 A1 | 2/2015 | Simon et al. |

FOREIGN PATENT DOCUMENTS

| WO | WO 2009/155723 A2 | 12/2009 |
| WO | WO 2010/090757 A1 | 8/2010 |
| WO | WO 2010/129959 A1 | 11/2010 |
| WO | WO 2011/050384 A2 | 5/2011 |

OTHER PUBLICATIONS

Suzuki et al. Broad Distribution of the JC Virus Receptor Contrasts with a Marked Cellular Restriction of Virus Replication. Virology 286: 100-112 (2001).*
Pastrana et al. Characterization of monoclonal antibodies specific for the Merkel cell polyomavirus capsid. Virology 405: 20-25 (2005).*
Murata et al. Identification of a neutralization epitope in the VP1 capsid protein of SV40.Virology. Nov. 10, 2008;381(1):116-22. Epub Sep. 11, 2008.*
Randhawa et al. Identification of species-specific and cross-reactive epitopes in human polyomavirus capsids using monoclonal antibodies. J Gen Virol. Mar. 2009;90(Pt 3):634-9.*
Chames et al. Therapeutic antibodies: successes, limitations and hopes for the future. British Journal of Pharmacology (2009), 157, 220-233.*
Gee et al., Modeling a sialic acid binding pocket in the external loops of JC virus VP1. J Biol Chem. Nov. 19, 2004;279(47

FIG. 1

Candidate Affinity ELISA

| | CH-P18C9 |
|---|---|
| Mad-1 | ≤0.1 |
| Type 3 | ≤0.1 |
| Type 1B | ≤0.1 |
| Type 2A | ≤0.1 |
| 269F-type 3 | ≤0.1 |
| 269Y-type 3 | 0.4 |
| 269F-type 1B | ≤0.1 |
| S267F | ≤0.1 |
| N265D | ≤0.1 |
| Q271H | ≤0.1 |
| D66H | ≤0.1 |
| K60E | 0.6 |
| K60N | ≤0.1 |
| L55F | ≤0.1 |

FIG. 2

Biacore Affinity Data

| $K_D$ (nM) | Type 1B wt | | Type 2A* wt | | MAD-1 wt | | Type 3 wt | | Type 3 S269F | | Type 3 269Y | | Type 3 L55F | |
|---|---|---|---|---|---|---|---|---|---|---|---|---|---|---|
| | Fab | mAb | Fab | mAb | Fab | mAb | Fab | mAb | Fab | mAb | Fab | mAb | Fab | mAb |
| P18C9 | | | 0.7 | 0.03 | 0.1 | 0.02 | 0.2 | 0.01 | >60 | ≤0.04 | >1450 | ≤0.6 | | |

| $K_D$ (nM) | Type 3 D66H | | Type 3 Q271H | | Type 3 K60E | | Type 3 N265D | | Type3 K60N | | Type3 S267F | | Type1B S269F | |
|---|---|---|---|---|---|---|---|---|---|---|---|---|---|---|
| | Fab | mAb

FIG. 4

Virus Preps

- Current purifications:
  - Benzonase/Neuraminidase Tx of CM
  - Spun thru 40% sucrose cushion
  - Resuspended: 0.01x original volume in HBSS++
  - Viruses:
    - 2Awt
    - 2A L55F
    - 2A N265D
    - 2A S269F • 2A S269Y
    - 2A K60E • 2A K60M
    - 2A S267F • 2A Q271F**
    - 2A D66H • 2A S61P
    - MAD1 (1Av wt)
    - All prep'd from post-infection material except ** were post-transfection
  - All titers (Geq) evaluated by qPCR

FIG. 5

Viral Mutant Infectivity: mAb Blocking assay

- Design:
  - 293ft cells: 96w format, 15e3 cells/well; Fn coated plates @ t= (-18hr)
  - 12 Viruses
    - 2A scaffold: wt, S269F, L55F, S269Y; K60E; K60M; S267F; N265D; Q271F; D66H; S61P
    - MAD1
    - 1.5e9GEq/well (MOI=1e5)
  - mAb
    - chi-18C9
    - 3-fold serial dilutions: 1000-0.46ng/ml final conc
  - 2 replicates ea condition per plate; 1 virus x 3mAbs per plate
  - Pre-inc virus + mAb 90min RT (low volume, 35ul)
  - Outgrow in presence mAb (@ appropriate conc, fv 100ul)
  - Aspirate media and replace with mAb supplemented media @ 3dpi, 7dpi
  - Harvest @ 11dpi
    - aspirate media, wash PBS-Ca++, Lyse in 100ul/well modified RIPA buffer (Y.Gao)
- Initial read-out:
  - Western (portion of 1 replicate ea condition)
    - All samples 7.5ul lysate/well
    - Detect with PAB597 1ug/ml O/N 4*C >> DαM-HRP 1::50K 90min >> detect Pierce SuperSignal West Dura ECL reagent

FIG. 7

Mutant Virus - mAb Protection Against Infection of 293ft:
S61P, D66H, N265D, S267F, Q271H, MAD1wt

FIG. 9

Mutant Virus - mAb Protection Against Infection of 293ft:
S61P, D66H, N265D, S267F, Q271H, MAD1wt

FIG. 10 chP18 Deamidation Mutants – Review/Summary

- Murine anti-VP1 monoclonal 18C9 selected as backup candidate based on VP1 mutant coverage
- Two “red-flags” addressed in context of the chimeric molecule: LC-C96, and HC N55G56
- First round: combos of WT, N55S, and N55Q HC with WT, C96S, C96A, and C96L LC expressed, purified and ELISA tested. Best of these was N55S/C96S - however lost 2-3 fold affinity on 269Y (3) and K60E (3), bringing those values above the minimal threshold of *0.3 nM*
- Round 2: N55D, H, A, L, T and G56V, P, and A paired with were LC-C96S purifed and tested on a subset of mutants; based on these results, N55N (WT) N55D, N55H, and N55S included in final big ELISA

FIG. 11

Purification of Round 2 ch18C9 Deamidation Mutants

- A portion of transient sup (50 or 100 ml) purified on protein A and SEC due to huge increase in binding observed with aggregated WT ch18C9 (AKTA Express, 2D mode)
- Five to 20 mg of each recovered from the two sups (not relevant to expression level – pA load close to capacity and concervative peak cutting on SEC)

SDS-PAGE:

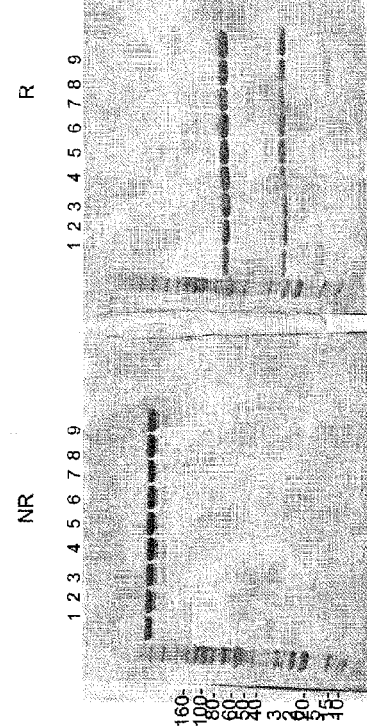

10 ul of each 1:5 dilution
NR - with NEM
R – with DTT

| 1 | ch18C9 N55D |
| 2 | ch18C9 N55H |
| 3 | ch18C9 N55A |
| 4 | ch18C9 G56V |
| 5 | ch18C9 N55 (wt) |
| 6 | ch18C9 G56P |
| 7 | ch18C9 N55L |
| 8 | ch18C9 N55T |
| 9 | ch18C9 G56A |

Analytical SEC:

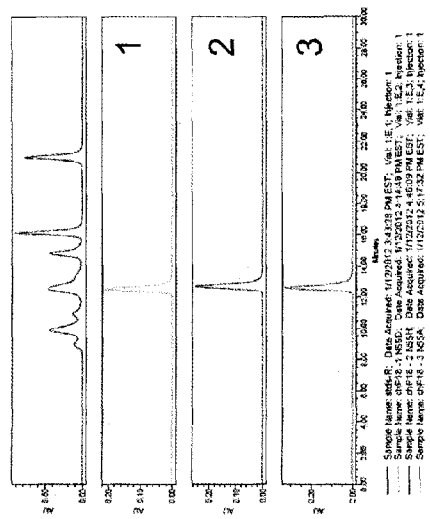

FIG. 14

Final ELISA's:
Select ch18C9 Variants on all Available VLP's

- ch18C9 variants:  HC-WT/LC-WT
  - HC-WT/LC-C96S
  - HC-N55D/LC-C96S
  - HC-N55H/LC-C96S
  - HC-N55S/LC-C96S

- VLP's (all prepared TFF/TMAE method unless * indicates hybrid UC/TMAE method:

| | | | | | |
|---|---|---|---|---|---|
| WT (1A) | | L55F(1B) | N265D (1B)* | | S269F (1B) |
| WT (1B) | | L55F (3) | N265D (3) | | S269F (3) |
| WT (2A) | | K60E (3) | S267F (1B) | | S269Y (1B)* |
| WT (2B) | | K60N (3) | S267F (3) | | S269Y (3) |
| WT (3) | D66H (1B) | | | Q271H (3) | |
| WT (Mad-1) | D66H (3) | | | | |

- 3-fold dilutions starting at 2 ug/ml (12 points) duplicate plates
- 10 or 20 plates per day; some VLP's duplicated from day to day to demonstrate reproducibiliy

FIG. 15

ELISA EC$_{50}$, nM

| | ch18C9 WT/WT | ch18C9 WT/C96S | ch18C9 N55D/C96S | ch18C9 N55H/C96S | ch18C9 N55S/C96S |
|---|---|---|---|---|---|
| WT (1A) | <0.1 | <0.1 | <0.1 | <0.1 | <0.1 |
| WT (1B) | <0.1 | <0.1 | <0.1 | <0.1 | <0.1 |
| WT (2A) | <0.1 | <0.1 | <0.1 | <0.1 | <0.1 |
| WT (2B) | <0.1 | <0.1 | <0.1 | <0.1 | <0.1 |
| WT (3) | <0.1 | <0.1 | <0.1 | <0.1 | <0.1 |
| WT (Mad-1) | <0.1 | <0.1 | <0.1 | <0.1 | <0.1 |
| L55F (1B) | <0.1 | <0.1 | <0.1 | <0.1 | <0.1 |
| L55F (3) | <0.1 | <0.1 | <0.1 | <0.1 | <0.1 |
| K60E (3) | 0.21 | 0.44 | 4.55 | <0.1 | 1.43 |
| K60N (3) | <0.1 | <0.1 | >>10 | <0.1 | <0.1 |
| D66H (1B) | <0.1 | <0.1 | <0.1 | <0.1 | <0.1 |
| D66H (3) | <0.1 | <0.1 | <0.1 | <0.1 | <0.1 |
| N265D (1B) | <0.1 | <0.1 | >10 | <0.1 | <0.1 |
| N265D (3) | <0.1 | <0.1 | 1 | <0.1 | <0.1 |
| S267F (1B) | <0.1 | <0.1 | 1.9 | <0.1 | <0.1 |
| S267F (3) | <0.1 | <0.1 | 0.12 | <0.1 | <0.1 |
| S269F (1B) | <0.1 | <0.1 | >10 | <0.1 | 0.2 |
| S269F (3) | <0.1 | <0.1 | >10 | <0.1 | <0.1 |
| S269Y (1B) | 2.2 | >10 | nb | <0.1 | >>10 |
| S269Y (3) | 0.3 | 0.4 | >>10 | <0.1 | 1.5 |
| Q271H (3) | <0.1 | <0.1 | <0.1 | <0.1 | <0.1 |

JCV NEUTRALIZING ANTIBODIES

RELATED APPLICATIONS

This application is a national stage filing under 35 U.S.C. §371 of international PCT application number PCT/US2013/031853, filed Mar. 15, 2013, which was published under PCT Article 21(2) in English, and claims the benefit under 35 U.S.C. §119 of U.S. provisional application No. 61/613,249, filed Mar. 20, 2012, the entire contents of each of which is incorporated herein by reference.

FIELD OF THE INVENTION

In one aspect, the disclosure relates to antibodies and uses thereof.

BACKGROUND

JC polyomavirus (JCV) is the causative agent of a demyelinating disease of the central nervous system, progressive multifocal leukoencephalopathy (PML). The incidence of PML can be related to a weakened immune system or treatment with immunosuppressants. Currently, there is no specific antiviral therapy that has been proven effective for treatment of PML.

SUMMARY OF THE INVENTION

In some embodiments, aspects of the invention relate to an isolated JC-virus neutralizing monoclonal antibody against JCV capsid protein VP1 (JCV-VP1). In some embodiments, the antibody suppresses infectivity of the JC-virus. In some embodiments, the antibody binds the sialic acid binding pocket of JCV-VP1.

In some embodiments, the antibody binds JCV-VP1 comprising one or more of the following mutations: S269F, S269Y, S267F, N265D, Q271H, D66H, K60E, K60N and L55F.

In some embodiments, the antibody binds JCV-VP1 comprising mutation S269F, JCV-VP1 comprising mutation S269Y, JCV-VP1 comprising mutation S267F, JCV-VP1 comprising mutation N265D, JCV-VP1 comprising mutation Q271H, JCV-VP1 comprising mutation D66H, and JCV-VP1 comprising mutation L55F.

In some embodiments, the JCV-VP1 is from JCV strain type 1a, 1b, 2a, 2b, 3, 4, or 7.

In some embodiments, the antibody comprises one or more of the following CDRs: CDR1: GYTLT (SEQ ID NO:48, h-18C9), CDR1: KASQDVGTAVA (SEQ ID NO:64, 1-18C9), CDR2: LINPYXXGTRYNQKFKG (SEQ ID NO:62, h-18C9 N55X N56X), CDR2: WASTRHT (SEQ ID NO:65, 1-18C9), CDR3: LGYYATGDEYFDY (SEQ ID NO:63, h-18C9), CDR3: QQYSSYPXT (SEQ ID NO:70, 1-18C9 C96X), and CDR sequences with up to two amino acid mutations as compared to SEQ ID NOs:48, 64, 62, 65, 63 and 70.

In some embodiments, the antibody comprises one or more of the following CDRs: CDR1: GYTLT (SEQ ID NO:48, h-18C9), CDR1: KASQDVGTAVA (SEQ ID NO:64, 1-18C9), CDR2: LINPYHGGTRYNQKFKG (SEQ ID NO:53, h-18C9 N55H), CDR2: WASTRHT (SEQ ID NO:65, 1-18C9), CDR3: LGYYATGDEYFDY (SEQ ID NO:63, h-18C9), CDR3: QQYSSYPST (SEQ ID NO:68, 1-18C9 C96S), and CDR sequences with up to two amino acid mutations as compared to SEQ ID NOs:48, 64, 53, 65, 63 and 68.

In some embodiments, the antibody comprises one or more of the following CDRs: CDR1: GYTLT (SEQ ID NO:48, h-18C9), CDR1: KASQDVGTAVA (SEQ ID NO:64, 1-18C9), CDR2: LINPYHGGTRYNQKFKG (SEQ ID NO:53, h-18C9 N55H), CDR2: WASTRHT (SEQ ID NO:65, 1-18C9), CDR3: LGYYATGDEYFDY (SEQ ID NO:63, h-18C9), CDR3: QQYSSYPST (SEQ ID NO:68, 1-18C9 C96S).

In some embodiments, the antibody comprises one or more of the following CDRs: CDR3: LGYYATGDEYFDY (SEQ ID NO:63, h-18C9), CDR3: QQYSSYPST (SEQ ID NO:68, 1-18C9 C96S), and CDR sequences with up to two amino acid mutations as compared to SEQ ID NOs: 63 and 68.

In some embodiments, the antibody comprises one or more of the following CDRs: CDR3: LGYYATGDEYFDY (SEQ ID NO:63, h-18C9), and CDR3: QQYSSYPST (SEQ ID NO:68, 1-18C9 C96S).

In some embodiments, the antibody comprises the following CDRs: CDR1: GYTLT (SEQ ID NO:48, h-18C9), CDR2: LINPYHGGTRYNQKFKG (SEQ ID NO:53, h-18C9 N55H), and CDR3: LGYYATGDEYFDY (SEQ ID NO:63, h-18C9).

In some embodiments, the antibody comprises the following CDRs: CDR1: KASQDVGTAVA (SEQ ID NO:64, 1-18C9), CDR2: WASTRHT (SEQ ID NO:65, 1-18C9), and CDR3: QQYSSYPST (SEQ ID NO:68, 1-18C9 C96S).

In some embodiments, the antibody comprises the following CDRs: CDR1: GYTLT (SEQ ID NO:48, h-18C9), CDR1: KASQDVGTAVA (SEQ ID NO:64, 1-18C9), CDR2: LINPYHGGTRYNQKFKG (SEQ ID NO:53, h-18C9 N55H), CDR2: WASTRHT (SEQ ID NO:65, 1-18C9), CDR3: LGYYATGDEYFDY (SEQ ID NO:63, h-18C9), and CDR3: QQYSSYPST (SEQ ID NO:68, 1-18C9 C96S).

In some embodiments, the antibody is humanized.

In some embodiments, the antibody is a chimeric antibody.

In some embodiments, the antibody comprises an IgG1 Fc-region.

In some embodiments, the antibody has effector function.

In some embodiments, the disclosure provides an isolated antibody comprising SEQ ID NO:23 (h-18C9 N55H) and SEQ ID NO:43 (1-18C9 C96S).

In some embodiments, the disclosure provides an isolated antibody comprising a sequence that has at least 80% homology to SEQ ID NO:23 (h-18C9 N55H) and a sequence that has at least 80% homology to SEQ ID NO:43 (1-18C9 C96S).

In some embodiments, the disclosure provides an isolated antibody comprising a sequence that has at least 90% homology to SEQ ID NO:23 (h-18C9 N55H) and a sequence that has at least 90% homology to SEQ ID NO:43 (1-18C9 C96S).

In some embodiments, the disclosure provides an isolated antibody comprising a sequence that has at least 95% homology to SEQ ID NO:23 (h-18C9 N55H) and a sequence that has at least 95% homology to SEQ ID NO:43 (1-18C9 C96S).

In some embodiments, the disclosure provides an isolated antibody comprising a sequence that has up to 10 mutations compared to SEQ ID NO:23 (h-18C9 N55H) and a sequence that has up to 10 mutations compared to SEQ ID NO:43 (1-18C9 C96S).

In some embodiments, the disclosure provides an isolated antibody having heavy chain sequence (SEQ ID NO: 71)
MDFGLSLVFLVLILKGVQCEVQLQQSGPELVKPGASMKISCKASGYSFTG
YTLTWVKQSHGKNLDWIGLINPYHGGTRYNQKFKGKATLTVDKSSSTAYM
ELLSLTSEDSAVYYCARLGYYATGDEYFDYWGQGTTLTVSSASTKGPSVF
PLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTC
PPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCS
VMHEALHNHYTQKSLSLSPG
and/or having light chain sequence (SEQ ID NO: 72)
MRVPAQLLGLLLLWLPGARCDIVMTQSHKFMSTSVGDRVSITCKASQDVG
TAVAWYQQKPGQSPKLLIYWASTRHTGVPDRFTGSRSGTDFTLTISNVQS
EDLADYFCQQYSSYPSTFGGGAKLEIRRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC.

In some embodiments, aspects of the invention relate to a method of treating a subject having one or more signs or symptoms of progressive multifocal leukoencephalopathy (PML), or having PML, the method comprising administering one or more of the antibodies described herein to a subject having one or more signs or symptoms of PML, or of having PML, in a therapeutically effective amount to treat PML.

In some embodiments, the antibody crosses the blood-brain barrier.

In some embodiments, the treatment results in a reduction in viral load, an improved EDSS score, an improved Karnofsky score, an improved MRI scan, or an improvement in cognition. In some embodiments, the subject is undergoing, or has been undergoing, immunotherapy treatment. In some embodiments, the subject is immunocompromised.

BRIEF DESCRIPTION OF THE DRAWINGS

The figures are illustrative only and are not required for enablement of the invention disclosed herein.

FIG. 1 shows the results of binding studies of antibody CH-P18C9 to a number of wild-type and mutant JCV-VP1 using ELISA.

FIG. 2 shows the results of binding studies of antibody P18C9 to a number of wild-type and mutant JCV-VP1 using Biacore.

FIG. 4 shows an overview of virus preps for infectivity assay.

FIG. 5 shows an overview of viral mutant infectivity assay.

FIG. 7 shows the results of the viral mutant infectivity assay as shown by Western blot.

FIG. 9 shows the results of the viral mutant infectivity assay as shown by Western blot.

FIG. 10 shows an overview of the generation of the antibody 18C9 mutants

FIG. 11 shows an overview of the purification of the antibody 18C9 mutants

FIG. 14 shows an overview of a JCV-VLP1 binding ELISA assay.

FIG. 15 shows results of a JCV-VLP1 binding ELISA assay.

DETAILED DESCRIPTION OF THE INVENTION

Figure 3:
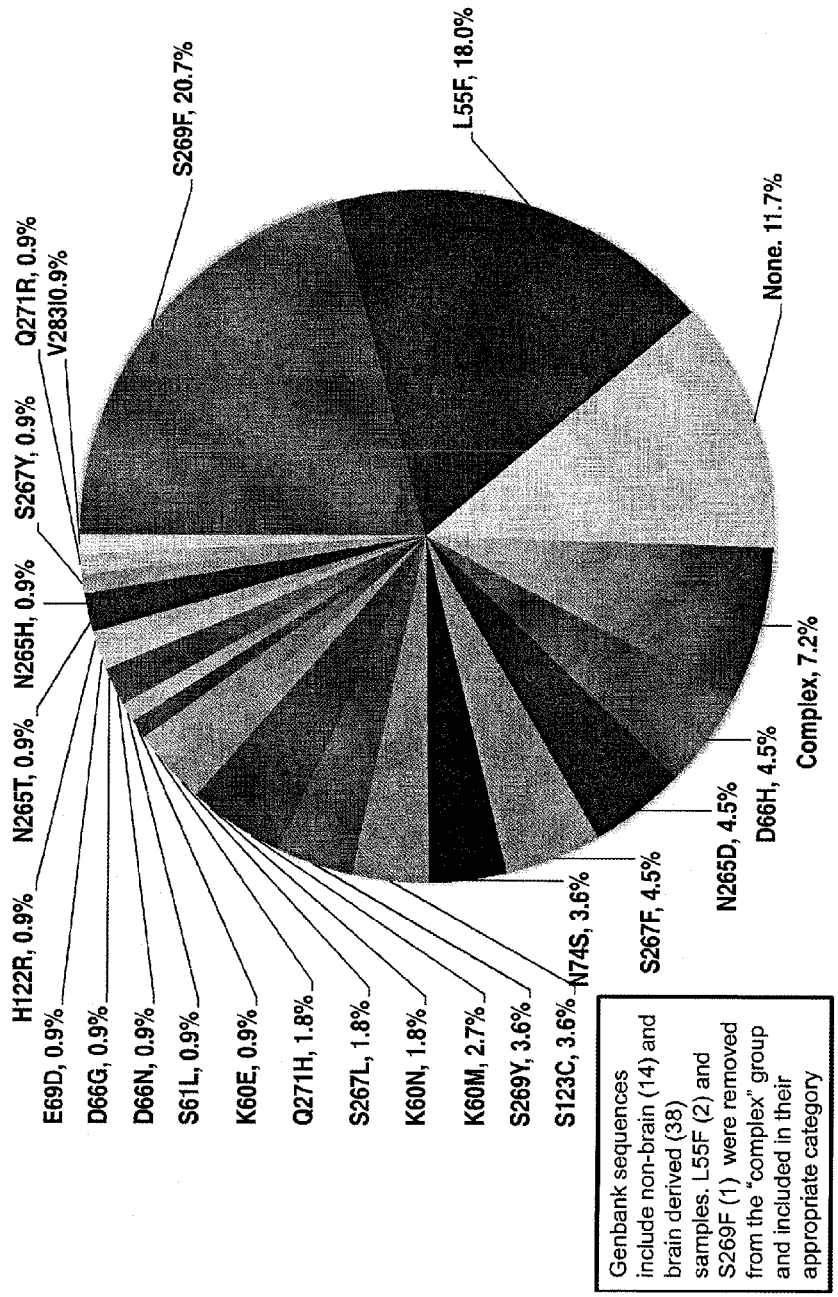
FIG. 3 provides an overview of the JCV VP1 combined mutation frequency.

In some embodiments, aspects of the invention relate to antibodies that bind to one or more JC Virus (JCV) proteins. In some embodiments, JCV-binding antibodies are neutralizing antibodies that reduce or inhibit one or more JCV functions. In some embodiments, a neutralizing antibody inhibits JCV replication, proliferation, and/or infectivity. In some embodiments, a neutralizing antibody induces viral clearance by the immune system, blocks virus receptor interactions, and/or disrupts virus capsids.

In some embodiments, antibodies that bind to a JCV coat protein, for example the JCV VP1 protein, are neutralizing antibodies. In some embodiments, antibodies that bind to the sialic acid binding pocket of the JCV VP1 protein are neutralizing antibodies. Surprisingly, a JCV neutralizing antibody that binds to VP1 can be effective against two or more different JCV variants, including variants that have one or more amino acid sequence changes within the sialic acid binding pocket of the VP1 protein.

A neutralizing antibody can be useful to help prevent, manage, and/or treat one or more conditions associated with a JCV infection. JCV infection is highly prevalent in humans. Primary infection with JCV can occur asymptomatically during childhood. JCV can be disseminated throughout the body, probably through viraemia and it is thought that JCV often persists mostly in brain and renal tissue. While infection by JCV is asymptomatic in most subjects, infection may result in serious conditions (like PML) and even death in some subjects. Subjects most susceptible to PML are subjects that are immuno-compromised (e.g., AIDS patients) or subjects undergoing treatment with immuno-suppressants (for instance after organ transplant or to treat an inflammation related condition such as multiple sclerosis). Neutralizing antibodies described herein can be used to treat patients that are at risk for developing a JCV associated condition. In some embodiments, an immuno-compromised patient can be treated with a JCV neutralizing antibody to reduce the risk of PML or other JCV-associated condition even if the treatment does not clear all JCV from the patient. It should be appreciated that by inhibiting JCV proliferation (e.g., JCV replication and/or dissemination in a subject), the risk of JCV-associated conditions can be reduced and/or managed as part of a treatment program for an immuno-compromised patient. In some embodiments, a patient receiving an immuno-suppressive drug (e.g., Tysabri) can be monitored for one or more signs or symptoms of a JCV-associated condition (e.g., PML). If a sign or symptom is detected, a JCV-neutralizing antibody can be administered. In some embodiments, the immuno-suppressive treatment also can be suspended or reduced to allow the patient's immune system to recover and counter a JCV infection or proliferation. However, it should be appreciated that a JCV-neutralizing antibody can be used in different therapeutic methods to treat or prevent JCV infections and/or JCV-associated conditions as described in more detail herein. It also should be appreciated that a JCV-neutralizing antibody can be used as a reagent, for example an assay reagent, to detect the presence of a JCV protein or virus in a sample. In some embodiments, antibodies described herein can be used as virus detection or quantification reagents.

In some embodiments, certain JCV variants are associated with an increased risk for a disease or disorder caused by the JCV infection. For example, certain mutations in the sialic acid binding pocket of the JCV VP1 protein have been associated with an increased risk for PML. In some embodiments, a JCV-neutralizing antibody is specific for one or more JCV variants. In some embodiments, a JCV-neutralizing antibody binds to a plurality of JCV variants with sufficient affinity to be therapeutically effective against those variants. In some embodiments, a JCV-neutralizing antibody binds to the sialic acid binding pocket of the JCV virus. It should be appreciated that the sialic acid binding pocket is reported to be the receptor interaction domain of the virus. In some embodiments, the sialic acid binding pocket includes amino acids 55-76 and amino acids 265-273 of JCV (See e.g., Gee et al., 2004, JBC 279: 49172-49176). In some embodiments, a JCV-neutralizing antibody binds to a plurality of JCV variants each having one or more amino acid changes within the sialic acid binding pocket. However, in some embodiments, certain amino acid changes within the sialic acid binding pocket reduce binding (and inhibition) by a JCV-neutralizing antibody. In some embodiments, a subject is screened for signs of a JCV infection. In some embodiments, a subject is screened for infection by a JCV variant. In some embodiments, a subject (for example a subject known to have a JCV infection) can be monitored for the appearance of one or more higher risk JCV variants. A positive result for JCV infection and/or the presence of certain JCV variants in a patient sample can be used as a basis for initiating treatment with a JCV-neutralizing antibody. However, it should be appreciated that in some embodiments a JCV-neutralizing antibody can be administered to a patient on the basis of an increased risk for JCV infection or proliferation and/or an increased risk for a JCV-associated condition, regardless of whether a JCV detection assay has been performed on the patient.

A reduction in JC Virus replication, proliferation, infectivity, and/or any other function caused by an antibody can be a measured (e.g., using an in vitro and/or in vivo assay) by comparing one or more JCV functions in the presence versus the absence of the antibody. In some embodiments, a neutralizing antibody can result in a reduction in one or more virus functions (e.g., replication, proliferation, infection, etc.) by about 5%, about 10%, about 20%, about 30%, about 40%, about 50%, about 60%, about 70%, about 80%, about 90%, about 95%, or more.

Antibodies:

In some embodiments, an antibody is a monoclonal antibody that is raised against a JCV VLP. In some embodiments, the antibody is specific for JCV. In some embodiments, the antibody is specific for JCV VP1.

In some embodiments, a neutralizing antibody that is specific for JCV has a neutralizing effect on JCV activity that is significantly higher than its neutralizing effect on the activity of one or more other viruses, for example, of a related virus (e.g., BK virus). However, in some embodiments, a neutralizing antibody may bind to one or more viruses with sufficient affinity to be useful to treat one or more different viral infections.

In some embodiments, the antibody is a monoclonal antibody. In some embodiments, the antibody is humanized. In some embodiments, an antibody has the sequence of 18C9 as described herein.

In some embodiments, an antibody comprises one or more of the following CDR sequences: CDR1: SEQ ID NOs:48, 64; CDR2: SEQ ID NOs:49-62, 65; CDR3: SEQ ID NOs:63, 66-70.

In some embodiments, an antibody comprises one or more of the following CDR sequences: CDR1: GYTLT (SEQ ID NO:48, h-18C9), CDR1: KASQDVGTAVA (SEQ ID NO:64, 1-18C9), CDR2: LINPYXXGTRYNQKFKG (SEQ ID NO:62, h-18C9 N55X N56X), CDR2: WASTRHT (SEQ ID NO:65, 1-18C9), CDR3: LGYYATGDEYFDY (SEQ ID NO:63, h-18C9), CDR3: QQYSSYPXT (SEQ ID NO:70, 1-18C9 C96X), and CDR sequences with up to two amino acid mutations as compared to SEQ ID NOs:48, 64, 62, 65, 63 and 70.

In some embodiments, an antibody comprises one or more of the following CDR sequences: CDR1: GYTLT (SEQ ID NO:48, h-18C9), CDR1: KASQDVGTAVA (SEQ ID NO:64, 1-18C9), CDR2: LINPYHGGTRYNQKFKG (SEQ ID NO:53, h-18C9 N55H), CDR2: WASTRHT (SEQ ID NO:65, 1-18C9), CDR3: LGYYATGDEYFDY (SEQ ID NO:63, h-18C9), CDR3: QQYSSYPST (SEQ ID NO:68, 1-18C9 C96S), and CDR sequences with up to two amino acid mutations as compared to SEQ ID NOs:48, 64, 53, 65, 63 and 68.

In some embodiments, an antibody comprises one or more of the following CDR sequences: CDR1: GYTLT (SEQ ID NO:48, h-18C9), CDR1: KASQDVGTAVA (SEQ ID NO:64, 1-18C9), CDR2: LINPYHGGTRYNQKFKG (SEQ ID NO:53, h-18C9 N55H), CDR2: WASTRHT (SEQ ID NO:65, 1-18C9), CDR3: LGYYATGDEYFDY (SEQ ID NO:63, h-18C9), CDR3: QQYSSYPST (SEQ ID NO:68, 1-18C9 C96S).

In some embodiments, an antibody comprises one or more of the following CDRs: CDR3: LGYYATGDEYFDY (SEQ ID NO:63, h-18C9), CDR3: QQYSSYPST (SEQ ID NO:68, 1-18C9 C96S), and CDR sequences with up to two amino acid mutations as compared to SEQ ID NOs: 63 and 68.

In some embodiments, an antibody comprises the following CDRs: GYTLT (SEQ ID NO:48, h-18C9), CDR2: LINPYHGGTRYNQKFKG (SEQ ID NO:53, h-18C9 N55H), and CDR3: LGYYATGDEYFDY (SEQ ID NO:63, h-18C9).

In some embodiments, an antibody comprises the following CDRs: CDR1: KASQDVGTAVA (SEQ ID NO:64, 1-18C9), CDR2: WASTRHT (SEQ ID NO:65, 1-18C9), and CDR3: QQYSSYPST (SEQ ID NO:68, 1-18C9 C96S).

In some embodiments, an antibody comprises one or more of the following CDRs: CDR1: GYTLT (SEQ ID NO:48, h-18C9), CDR1: KASQDVGTAVA (SEQ ID NO:64, 1-18C9), CDR2: LINPYHGGTRYNQKFKG (SEQ ID NO:53, h-18C9 N55H), CDR2: WASTRHT (SEQ ID NO:65, 1-18C9), CDR3: LGYYATGDEYFDY (SEQ ID NO:63, h-18C9), and CDR3: QQYSSYPST (SEQ ID NO:68, 1-18C9 C96S).

In some embodiments, an antibody has the following heavy chain CDR3: LGYYATGDEYFDY (SEQ ID NO:63, h-18C9), and/or the following light chain CDR3: QQYSSYPST (SEQ ID NO:68, 1-18C9 C96S).

In some embodiments, an antibody has the following heavy chain CDR2: LINPYHGGTRYNQKFKG (SEQ ID NO:53, h-18C9 N55H), and/or the following light chain CDR2: WASTRHT (SEQ ID NO:65, 1-18C9).

In some embodiments, an antibody has the following heavy chain CDR1: GYTLT (SEQ ID NO:48, h-18C9), and/or the following light chain CDR1: KASQDVGTAVA (SEQ ID NO:64, 1-18C9), In some embodiments, an antibody has a heavy chain variable region having one of the following SEQ ID NOs:9, 10, 16-39. In some embodiments, an antibody has a light chain variable region having one of the following SEQ ID NOs:11,12, 40-47

In some embodiments, an antibody has a heavy chain variable region having SEQ ID NO:23 (h-18C9 N55H). In some embodiments, an antibody has a light chain variable region having SEQ ID NO:43 (1-18C9 C96S).

In some embodiments, an antibody may be substantially a full length VP-1 binding antibody or a functional fragment thereof. For example, if a fragment of a VP-1 binding antibody is sufficient to allow specific binding by an antibody that specifically binds a VP-1 binding antibody it is a functional VP-1 binding antibody and may be used in the methods and kits of the invention. In some embodiments, an antibody fragment can be used if it provides sufficient binding to inhibit JCV function and/or to be useful as a detection agent for JCV. One of ordinary skill in the art will be able to identify VP-1 binding antibody fragments and determine whether a VP-1 binding antibody fragment is a functional VP-1 binding antibody fragment using only routine procedures and binding assays (e.g., competition assays using a substantially full length VP-1 binding antibody described herein.

In some embodiments, an antibody may be a chimeric antibody that contains a variable region (e.g., a humanized variable region) from a first species (e.g., a mouse) and an Fc region from a second species (e.g., a human). As will be apparent to one of ordinary skill in the art, the present invention also provides for F(ab')2, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences.

In certain embodiments, a JCV neutralizing antibody may be an anti-VP1 single-chain antibody, a single-domain antibody, or a Nanobody™. Characteristics of each of these antibody types and methods for their use are well known in the art. Nanobodies™ are the smallest functional fragments of antibodies and are derived from naturally occurring single-chain antibodies (see Ablynx, Belgium; ablynx.com). Nanobody™ technology was developed following the discovery that camelidae (camels and llamas) possess a unique repertoire of fully functional antibodies that lack light chains. Nanobody™ structure consists of a single variable domain (VHH), a hinge region, and two constant domains (CH2 and CH3). The cloned and isolated VHH domain is a stable polypeptide harboring the full antigen-binding capacity of the original heavy chain. Nanobodies™ combine the features of conventional antibodies with features of small molecule drugs. Nanobodies™ show high target specificity and low inherent toxicity. Additionally, Nanobodies™ are very stable, can be administered by means other than injection, and are easy to manufacture. In certain embodiments, a therapeutic JCV neutralizing antibody, an immobilization moiety, and/or a detection moiety may be a humanized Nanobody™.

In some embodiments, an exemplary JCV neutralizing antibody has one or more CDRs, e.g., all three Heavy Chain (HC) CDRs and/or all three Light Chain (LC) CDRs of a particular antibody disclosed herein, or CDRs that are, in sum, at least 80, 85, 90, 92, 94, 95, 96, 97, 98, or 99% identical to such an antibody, e.g., CDR1: SEQ ID NOs:48 and 64; CDR2: SEQ ID NOs:49-62 and 65; CDR3: SEQ ID NOs:63, 66-70. In some embodiments, an exemplary JCV neutralizing antibody has one, two three, four, five or six of the CDRs, e.g., all three Heavy Chain (HC) CDRs and/or all three Light Chain (LC) CDRs of a particular antibody disclosed herein. In some embodiments, an exemplary JCV neutralizing antibody has one or more CDRs, e.g., all three HC CDRs and/or all three LC CDRs of a particular antibody disclosed herein, or CDRs that include one, up to two, up to three, up to four, up to five, up to six, up to seven, up to eight, up to nine or up to ten amino acid changes compared to e.g., CDR1: SEQ ID NOs:48 and 64; CDR2: SEQ ID NOs:49-62 and 65 CDR3: SEQ ID NOs:63, 66-70. In one embodiment, the H1 and H2 hypervariable loops have the same canonical structure as those of an antibody described herein. In one embodiment, the L1 and L2 hypervariable loops have the same canonical structure as those of an antibody described herein.

In one embodiment, the amino acid sequence of the HC and/or LC variable domain sequence is at least 70, 80, 85, 90, 92, 95, 97, 98, 99, or 100% identical to the amino acid sequence of the Heavy Chain (HC) and/or Light Chain (LC) variable domain of an antibody described herein, e.g., SEQ ID NOs: 1-47. The amino acid sequence of the HC and/or LC variable domain sequence can differ by at least one amino acid, but no more than ten, eight, six, five, four, three, or two amino acids from the corresponding sequence of an antibody described herein, e.g., SEQ ID NOs: 1-47. For example, the differences may be primarily or entirely in the framework regions.

The amino acid sequences of the HC and LC variable domain sequences can be encoded by a sequence that hybridizes under high stringency conditions to a nucleic acid sequence described herein or one that encodes a variable domain or to a nucleic acid encoding an amino acid sequence described herein. In one embodiment, the amino acid sequences of one or more framework regions (e.g., FR1, FR2, FR3, and/or FR4) of the HC and/or LC variable domain are at least 70, 80, 85, 90, 92, 95, 97, 98, 99, or 100% identical to corresponding framework regions of the HC and LC variable domains of an antibody described herein. In one embodiment, one or more heavy or light chain framework regions (e.g., HC FR1, FR2, and FR3) are at least 70, 80, 85, 90, 95, 96, 97, 98, or 100% identical to the sequence of corresponding framework regions from a human germline antibody.

Calculations of "homology" or "sequence identity" between two sequences (the terms are used interchangeably herein) can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

The skilled artisan will realize that conservative amino acid substitutions may be made in JCV neutralizing antibodies to provide functionally equivalent variants of these antibodies, e.g., the variants retain the functional capabilities of inhibiting one or more JCV functions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Exemplary functionally equivalent variants of JCV neutralizing antibodies include conservative amino acid substitutions of in the amino acid sequences of proteins disclosed herein. Conservative substitutions of amino acids include substitutions made amongst amino acids within the following groups: (a) M, I, L, V; (b) F, Y5 W; (c) K, R, H; (d) A, G; (e) S, T; (f) Q, N; and (g) E, D.

As used herein, the term "hybridizes under high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and non-aqueous methods are described in that reference and either can be used. High stringency hybridization conditions can include hybridization in 6×SSC at about 45° C., followed by one or more washes in 0.2×SSC, 0.1% SDS at 65° C., or substantially similar conditions.

Antibodies can be tested for a functional property, for example, JCV neutralization, e.g., as described herein or using other techniques for evaluating JCV replication, propagation, infectivity, and/or other function.

In some embodiments, a combination of two or more different antibodies may be used. In some embodiments, one or more antibodies may be used in combination with one or more other agents. In some embodiments, tetravalent antibodies, antibodies coupled to blood brain barrier transporters, antibodies coupled to contrast dye reagents, and/or radiolabelled antibodies can be used (e.g., as markers of JCV presence in patients).

Obtaining Antibodies and Antigen Binding Fragments:

JCV neutralizing antibodies can be generated by immunization, e.g., using an animal such as a mouse. A JCV VLP, or a VLP protein (e.g., VP1) can be used as an immunogen. In some embodiments, a VLP or VLP protein having a wild-type or normal sequence can be used. In some embodiments, a VLP or VLP protein having one or more mutations (for example in the sialic acid binding pocket of VP1) can be used as an immunogen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). Antibodies or immunoglobulins include broad classes of polypeptides that can be distinguished biochemically. Those skilled in the art will appreciate that heavy chains are classified as gamma, mu, alpha, delta, or epsilon, with some subclasses among them (e.g., gamma1-gamma4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and JCV neutralizing antibodies of different classes can be obtained or engineered as described herein. It should be appreciated that all immunoglobulin classes are within the scope of the present invention. However, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda. Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As described herein, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a beta-sheet conformation and the CDRs form loops which connect, and in some cases form part of, the beta-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196:901-917 (1987), which are incorporated herein by reference in their entireties).

It should be appreciated that antibodies obtained as described herein can be altered to remove or replace one or more CDRs. In some embodiments, antigen binding fragments can be generated that retain antigen specificity but that lack one or more of the six CDRs of a full-length antibody. Alternatively, one or more CDRs from an antibody can be retained (for example CDR3) and one or more of the other CDRs can be engineered and or replaced with a different CDR, for example, to alter antigen binding specificity and/or affinity.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in a neutralizing antibody or antigen-binding fragment, variant, or derivative thereof of the present invention are according to the Kabat numbering system.

In camelid species, the heavy chain variable region, referred to as VHH, forms the entire antigen-binding domain. The main differences between camelid VHH variable regions and those derived from conventional antibodies (VH) include (a) more hydrophobic amino acids in the light chain contact surface of VH as compared to the corresponding region in VHH, (b) a longer CDR3 in VHH, and (c) the frequent occurrence of a disulfide bond between CDR1 and CDR3 in VHH.

As described herein, JCV binding antibodies or antigen-binding fragments, variants, or derivatives thereof include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to neutralizing antibodies disclosed herein). ScFv molecules are known in the art and are described, e.g., in U.S. Pat. No. 5,892,019. JCV neutralizing immunoglobulin or antibody molecules can be of any type (e.g., IgG, IgE, IgM, IgD, IgA, and IgY), class (e.g., IgG1, IgG2, IgG3, IgG4, IgA1 and IgA2) or subclass of immunoglobulin molecule.

JCV neutralizing antibody fragments, including single-chain antibodies, may comprise the variable region(s) alone or in combination with the entirety or a portion of the following: hinge region, CH1, CH2, and CH3 domains. Also, JCV neutralizing antigen-binding fragments can comprise any combination of variable region(s) with a hinge region, CH1, CH2, and CH3 domains.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

As used herein, the term "light chain portion" includes amino acid sequences derived from an immunoglobulin light chain. Preferably, the light chain portion comprises at least one of a VL or CL domain.

Neutralizing antibodies, or antigen-binding fragments, variants, or derivatives thereof disclosed herein may be described or specified in terms of the epitope(s) or portion(s) of an antigen, e.g., a target polypeptide of the JCV VP1 protein that they recognize or specifically bind. The portion of a target polypeptide which specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or include non-polypeptide elements, e.g., an "epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In some embodiments, a peptide or polypeptide epitope recognized by neutralizing antibodies described herein contains a sequence of at least 4, at least 5, at least 6, at least 7, more preferably at least 8, at least 9, at least 10, at least 15, at least 20, at least 25, or between about 15 to about 30 contiguous or non-contiguous amino acids of a JCV VLP protein (e.g., VP1). (See e.g., WO2010/090757)

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Neutralizing antibodies or antigen-binding fragments, variants or derivatives thereof described herein may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Neutralizing antibodies or antigen-binding fragments, variants or derivatives thereof described herein may also be described or specified in terms of their binding affinity to a polypeptide. For example, a JCV neutralizing antibody may bind to a JCV peptide (e.g., a VP1 peptide) with a dissociation constant or Kd less than $10^{-2}$M, $10^{-3}$M, $10^{-4}$M, $10^{-5}$M, $10^{-6}$M, $10^{-7}$M, $10^{-8}$M, $10^{-9}$M, $10^{-10}$M, $10^{-11}$M, $10^{-12}$M, $10^{-13}$M, $10^{-14}$M, or $10^{-15}$M.

Neutralizing antibodies or antigen-binding fragments, variants or derivatives thereof described herein may be "multispecific," e.g., bispecific, trispecific or of greater multispecificity, meaning that it recognizes and binds to two or more different epitopes present on one or more different antigens (e.g., proteins) at the same time. Thus, whether a neutralizing antibody is "monospecific" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

Humanization:

In some embodiments, an animal antibody (e.g., mouse antibody) can be modified, for example by, exchanging the Fc region with an Fc region from a different species (for example with a human Fc region). In some embodiments, one or more humanization changes also may be made (for example in one or more of the framework regions of the antibody).

In some embodiments, antibodies described herein may be engineered, by partial framework region replacement and sequence changing. In some embodiments, CDRs are derived from an antibody of a different class and/or a different species than the framework regions. In some embodiments, an engineered antibody contains one or more "donor" CDRs from a non-human antibody of known specificity that are grafted into a human heavy or light chain framework region. It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

EP 239 400 (Winter et al.) describes altering antibodies by substitution (within a given variable region) of their complementarity determining regions (CDRs) for one species with those from another. CDR-substituted antibodies are predicted to be less likely to elicit an immune response in humans compared to true chimeric antibodies because the CDR-substituted antibodies contain considerably less non-human components. (Riechmann et al., 1988, Nature 332, 323-327; Verhoeyen et al., 1988, Science 239, 1534-1536). Typically, CDRs of a murine antibody substituted into the corresponding regions in a human antibody by using recombinant nucleic acid technology to produce sequences encoding the desired substituted antibody. Human constant region gene segments of the desired isotype (usually gamma I for CH and kappa for CL) can be added and the humanized heavy and light chain genes are co-expressed in mammalian cells to produce soluble humanized antibody.

Queen et al., 1989 Proc Natl Acad Sci USA. December; 86(24): 10029-33 and WO 90/07861 have described a process that includes choosing human V framework regions by computer analysis for optimal protein sequence homology to the V region framework of the original murine antibody, and modeling the tertiary structure of the murine V region to visualize framework amino acid residues which are likely to interact with the murine CDRs. These murine amino acid residues are then superimposed on the homologous human framework. See also U.S. Pat. Nos. 5,693,762; 5,693,761; 5,585,089; and 5,530,101. Tempest et al., 1991, Biotechnology 9, 266-271) utilize, as standard, the V region frameworks derived from NEWM and REI heavy and light chains respectively for CDR-grafting without radical introduction of mouse residues. An advantage of using the Tempest et al., approach to construct NEWM and REI based humanized antibodies is that the three-dimensional structures of NEWM and REI variable regions are known from x-ray crystallography and thus specific interactions between CDRs and V region framework residues can be modeled. However, it should be appreciated that similar approaches may be based on one or more other known antibody structures (e.g., based on one or more Fab structures). In some embodiments, a human germline framework may be used In some embodiments, a mouse VH region (e.g., the 18C9 antibody described herein) has a framework 1 and/or a framework 3 that is shorter than the corresponding human framework regions. In some embodiments, corresponding amino acid deletions can be made in humanized variants of mouse antibodies. In some embodiments, these deletions do not have a large effect on affinity Non-human antibodies can be modified to include substitutions that insert human immunoglobulin sequences, e.g., consensus human amino acid residues at particular positions, e.g., at one or more of the following positions (preferably at least five, ten, twelve, or all): (in the FR of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the FR of the variable domain of the heavy chain) 2H, 4H, 24H, 36H, 37H, 39H, 43H, 45H, 49H5 58H, 6OH, 67H, 68H, 69H, 7OH, 73H, 74H, 75H, 78H, 91H, 92H, 93H, and/or 103H (according to the Kabat numbering). See, e.g., U.S. Pat. No. 6,407,213.

Antibody Production:

Monoclonal (e.g., monoclonal rabbit, mouse, chimeric, humanized, fully human, etc.) JCV neutralizing antibodies can be produced using techniques known in the art. In some embodiments, fully human antibodies can be produced, e.g., using in vitro-primed human splenocytes, as described by Boerner et al., 1991, J. Immunol., 147, 86-95. They may be prepared by repertoire cloning as described by Persson et al., 1991, Proc. Nat. Acad. Sci. USA, 88: 2432-2436 or by Huang and Stollar, 1991, J. Immunol. Methods 141, 227-236. U.S. Pat. No. 5,798,230. Large nonimmunized human phage display libraries may also be used to isolate high affinity antibodies that can be developed as human therapeutics using standard phage technology (see, e.g., Vaughan et al, 1996 Nat Biotechnol. March; 14(3):309-14; Hoogenboom et al. (1998) Immunotechnology 4:1-20; and Hoogenboom et al. (2000) Immunol Today 2:371-8; US Published Patent Application No. 2003-0232333). Antibodies can be produced in prokaryotic and eukaryotic cells. In some embodiments, antibodies (e.g., scFvs) are expressed in a yeast cell such as *Pichia* (see, e.g., Powers et al. (2001) J Immunol Methods. 251:123-35), *Hanseula*, or *Saccharomyces*.

In some embodiments, antibodies, particularly full length antibodies, e.g., IgGs, are produced in mammalian cells. Exemplary mammalian host cells for recombinant expression include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) MoI. Biol. 159:601-621), lymphocytic cell lines, e.g., NSO myeloma cells and SP2 cells, COS cells, K562, and a cell from a transgenic animal, e.g., a transgenic mammal. For example, a mammary epithelial cell can be used.

In addition to the nucleic acid sequence(s) encoding the immunoglobulin domain, recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). Exemplary selectable marker genes include the dihydrofolate reductase (DHFR) gene (for use in dhfr-host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. For example, some antibodies can be isolated by affinity chromatography with a Protein A or Protein G. In some embodiments, mouse antibody variable regions were cloned and expressed in CHO cells.

Antibodies also can include modifications, e.g., modifications that alter Fc function, e.g., to decrease or remove interaction with an Fc receptor or with Clq, or both. For example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some antibodies that include an Fc domain, the antibody production system may be designed to synthesize antibodies in which the Fc region is glycosylated. For example, the Fc domain of IgG molecules is glycosylated at asparagine 297 in the CH2 domain. This asparagine is the site for modification with biantennary-type oligosaccharides. This glycosylation participates in effector functions mediated by Fcγ receptors and complement Clq (Burton and Woof (1992) Adv. Immunol. 51:1-84; Jefferis et al. (1998) Immunol. Rev. 163:59-76). The Fc domain can be produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method for expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

In certain embodiments, rather than humanizing an existing antibody or antigen binding fragment from a different species, an animal that contains immunoglobulin producing cells having natural, human, or partially human immunoglobulin loci can be immunized. In some embodiments, the non-human animal includes at least a part of a human immunoglobulin gene. For example, it is possible to engineer animal strains that are deficient in animal antibody production using large fragments of the human Ig loci. Using the hybridoma technology, antigen-specific monoclonal antibodies derived from the genes with the desired specificity may be produced and selected.

Therapeutic Applications:

In some embodiments, a neutralizing antibody described herein may be administered to a subject who is undergoing a therapy with an immunosuppressive drug. In some embodiments, a JCV neutralizing antibody may be used to prevent the development or progression of PML in a subject that is undergoing treatment for multiple sclerosis (MS). For example, a subject undergoing treatment with natalizumab or a related VLA-4 binding antibody may be a candidate for treatment with a JCV neutralizing antibody.

Natalizumab and related VLA-4 binding antibodies are described, e.g., in U.S. Pat. No. 5,840,299. mAb 21.6 and HP 1/2 are exemplary murine monoclonal antibodies that bind VLA-4. Natalizumab is a humanized version of murine mAb 21.6 (see, e.g., U.S. Pat. No. 5,840,299). A humanized version of HP1/2 has also been described (see, e.g., U.S. Pat. No. 6,602,503). Several additional VLA-4 binding monoclonal antibodies, such as HP2/1, HP2/4, L25 and P4C2, are described (e.g., in U.S. Pat. No. 6,602,503; Sanchez-Madrid et al., 1986 Eur. J. Immunol, 16:1343-1349; Hemler et al., 1987 J. Biol. Chem. 2:11478-11485; Issekutz and Wykretowicz, 1991, J. Immunol, 147: 109 (TA-2 mab); Pulido et al, 1991 J. Biol. Chem., 266(16):10241-10245; and U.S. Pat. No. 5,888,507). Many useful VLA-4 binding antibodies interact with VLA-4 on cells, e.g., lymphocytes, but do not cause cell aggregation. However, other anti-VLA-4 binding antibodies have been observed to cause such aggregation. HP1/2 does not cause cell aggregation. The HP1/2 MAb (Sanchez-Madrid et al., 1986 Eur. J. Immunol., 16:1343-1349) has an extremely high potency, blocks VLA-4 interaction with both VCAM1 and fibronectin, and has the specificity for epitope B on VLA-4. This antibody and other B epitope-specific antibodies (such as B1 or B2 epitope binding antibodies; Pulido et al., 1991 J. Biol. Chem., 266(16):10241-10245) represent one class of useful VLA-4 binding antibodies.

In some embodiments, a subject is human. In some embodiments, a subject is a non-human animal, for example a non-human mammal (e.g., mouse, rat, rabbit, goat, etc.).

Applications:

In some embodiments, a neutralizing antibody can be administered to a subject to prevent or treat a JC Virus infection, and/or to prevent or treat PML.

In some embodiments, aspects of the invention relate to antibody compositions that inhibit JC Virus activity, for example, that inhibit one or more of viral proliferation (e.g., viral replication), mutation rate, and infectivity. In some embodiments, such compositions can be used to treat or suppress conditions associated with JC Virus activity in subjects that are infected with a JC Virus, or to lower the risk of infection with the JC Virus. Such compositions may be used to prevent JCV viral infection, to prevent an increase in JCV viral activity (e.g., active JCV infection of the brain), to prevent JC Virus proliferation, to prevent symptoms associated with viral infection, to treat a subject infected with a JC Virus, or treat a subject at risk of infection with a JC Virus, or to treat a subject that has developed a disease or condition associated with infection by a JC Virus (e.g., PML). Compositions of the invention also may be administered to a subject at risk of a viral infection or at risk of an increase in viral activity (e.g., viral proliferation, for example in the brain or CNS), regardless of whether the subject is actually known to have been exposed to, or infected by, the virus.

In some embodiments, one or more antibody compositions can be administered to subjects that have a compromised immune system. It should be appreciated that a subject's immune system may be compromised due to treatment with an immunosuppressive therapeutic agent and/or due to a disease or condition that impacts the immune system. In some embodiments, one or more antibody compositions can be administered to a subject that is at risk of PML due to a compromised immune system, regardless of whether the subject is known to be infected with JCV or known to have been exposed to JCV. Accordingly, compositions of the invention may be administered to subjects that are receiving an immunosuppressive treatment for a disease or condition. In some embodiments, compositions of the invention may be administered to multiple sclerosis (MS) patients that are being treated with one or more immunosuppressive agents (e.g., natalizumab). However, in some embodiments, compositions of the invention may be administered to subjects that have a weakened immune system caused by a disease or condition itself, rather than by an immunosuppressive treatment. For example, subjects infected with an immuno-compromising pathogen (e.g., a virus such as HIV) may be treated with one or more antibody compositions described herein.

It should be appreciated that while the JCV status of a subject need not be known, it may be useful to know the status in some embodiments. In some embodiments, the efficacy of such treatment or therapy may be monitored by detecting and/or monitoring the presence of JCV in a subject.

In some embodiments, one or more antibody compositions can be administered to a subject before, during, and/or after the subject receives and immunomodulatory therapy (e.g., a treatment that inhibits the immune system of the subject). Accordingly, in some embodiments one or more compounds described herein as being effective to inhibit JC Virus replication may be administered to a subject prior to initiation of an immunomodulatory therapy. For example, a therapeutic regimen of one or more compositions of the invention may be initiated prior to an immunomodulatory treatment against a disease or in preparation for a transplant in to prevent or reduce any risk of JC Virus replication or proliferation associated with the immunomodulatory treatment.

In some embodiments, one or more compositions of the invention may be administered alone or in combination with other compositions described herein or along with other therapeutic agents (e.g., one or more immunosuppressive therapeutic agents). Compositions of the invention may be provided (e.g., administered) in pharmaceutical preparations. Compositions of the invention may be provided in kits.

In some embodiments, a subject that is being treated with (or that is going to start a treatment with) an immunosuppressive agent is tested for one or more indicia of JCV infection. If one or more indicia of JCV infection are detected, the subject may be evaluated for the presence of one or more JCV variants associated with PML as described herein. If no indicia for JCV are detected, the subject may be monitored over time, e.g., every 4 weeks, monthly, every three months, every 4 months, every 6 months, or every 12 months, for the presence of any indicia of JCV infection. If a JCV infection is detected, the subject may be further evaluated for the presence of one or more JCV variants. If a JCV variant associated with increased PML risk is detected, the subject may be further monitored to detect any early signs of PML and/or the treatment regimen may be altered as described in more detail herein.

In some embodiments, a neutralizing antibody can be useful to slow the progression of a condition (e.g., PML) that is associated with a JCV infection. In some embodiments, a delay in the progression of PML or other condition associated with JCV allows a subject's immune response to fight the JCV infection. For example, if a subject undergoing immunotherapy or treatment with a drug that is immunosuppressive, is diagnosed as having a JCV infection, and/or as having one or more signs or symptoms of PML (e.g., early stage PML), then the subject can be treated by administering one or more antibody compositions described herein. In some embodiments, treatment with the immunotherapy or drug that is immunosuppressive is reduced or stopped during the time that the JCV neutralizing antibody is administered. This can allow the immune system of the subject to recover and help fight off the JCV infection or disease progression.

Nucleic Acids Encoding the Antibodies:

In some embodiments, the following nucleic acid sequence was used to encode a neutralizing antibody heavy chain:

(SEQ ID NO: 73)
atggacttcggggttgagcttggttttccttgtcctaattttaaaaggtgt ccagtgtgaagtgcagctgcagcagtccggccctgagctggtgaaacctg gcgcctccatgaagatcagctgcaaggcctccggctactccttcaccggc tacaccctgacctgggtgaaacagtcccacggcaagaacctggactggat cggcctgatcaacccctaccacggcggcacccggtacaaccagaagttca agggcaaggccaccctgaccgtggacaagtcctcctccaccgcctacatg gaactgctgtccctgacctccgaggactccgccgtgtactactgcgccag actgggctactacgccaccggcgacgagtacttcgactactggggccagg gcaccaccctgacagtgtcctccgcctctaccaagggcccctccgtgttc cctctggccccctccagcaagtccacctctggcggcaccgccgctctggg ctgcctggtcaaggactacttccccgaaccggtgacggtgtcgtggaact caggcgccctgaccagcggcgtgcacaccttcccggctgtcctacagtcc tcaggactctactccctcagcagcgtggtgaccgtgccctccagcagctt gggcacccagacctacatctgcaacgtgaatcacaagcccagcaacacca aggtggacaagaaagttgagcccaaatcttgtgacaagactcacacatgc ccaccgtgcccagcacctgaactcctgggggaccgtcagtcttcctctt cccccaaaacccaaggacaccctcatgatctcccggacccctgaggtca catgcgtggtggtggacgtgagccacgaagaccctgaggtcaagttcaac tggtacgtggacggcgtggaggtgcataatgccaagacaaagccgcggga ggagcagtacaacagcacgtaccgtgtggtcagcgtcctcaccgtcctgc accaggactggctgaatggcaaggagtacaagtgcaaggtctccaacaaa gccctcccagcccccatcgagaaaaccatctccaaagccaaagggcagcc ccgagaaccacaggtgtacaccctgcccccatcccgggatgagctgacca agaaccaggtcagcctgacctgcctggtcaaaggcttctatcccagcgac atcgccgtggagtgggagagcaatgggcagccggagaacaactacaagac cacgcctcccgtgttggactccgacggctccttcttcctctacagcaagc tcaccgtggacaagagcaggtggcagcaggggaacgtcttctcatgctcc gtgatgcatgaggctctgcacaaccactacacgcagaagagcctctccct gtctccggt In some embodiments, the following nucleic acid sequence was used to encode a neutralizing antibody light chain:

(SEQ ID NO: 74)
atgagggtccccgctcagctcctggggctccttctgctctggctccctgg agccagatgtgacatcgtgatgacccagtcccacaagttcatgtccacct ccgtgggcgaccgggtgtccatcacatgcaaggcctcccaggacgtgggc accgccgtggcctggtatcagcagaagcccggccagtcccccaagctgct gatctactgggcctccaccagacacaccggcgtgcccgacagattcaccg gctccagatccggcaccgacttcacccctgaccatctccaacgtgcagtcc gaggacctggccgactacttctgccagcagtactcctcctacccccagcac cttcggcggaggcgccaagctggaaatccggcgtacggtggctgcaccat -continued

```
ctgtcttcatcttcccgccatctgatgagcagttgaaatctggaactgcc tctgttgtgtgcctgctgaataacttctatcccagagaggccaaagtaca gtggaaggtggataacgccctccaatcgggtaactcccaggagagtgtca cagagcaggacagcaaggacagcacctacagcctcagcagcaccctgacg ctgagcaaagcagactacgagaaacacaaagtctacgcctgcgaagtcac ccatcagggcctgagctcgcccgtcacaaagagcttcaacaggggagagt gt.
```

Cell Lines Useful for Expressing the Antibodies:

In some embodiments, one or more neutralizing antibodies can be express in CHO or HEK293 cells. However, any suitable cell line may be used as aspects of the invention are not limited in this respect.

Administration Routes:

In some embodiments, the invention provides methods of inhibiting viral replication, the methods comprising contacting a cell comprising a JC Virus with an antibody composition.

In certain embodiments, an antibody or antibody preparation is administered intravenously. In other embodiments, an antibody or antibody preparation is administered orally. Alternative routes of administration include sublingual, intramuscular, and transdermal administrations. Accordingly, preparations of the present invention may be given orally, parenterally, topically, or rectally. They are of course given in forms suitable for each administration route.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of an antibody, drug or other material other than directly into the central nervous system, such that it enters the patient's system and, thus, is subject to metabolism and other like processes, for example, subcutaneous administration.

Antibody compositions may be administered to humans and other animals for therapy by any suitable route of administration. Actual dosage levels of neutralizing antibodies may be adjusted to obtain an amount that is effective to achieve the desired therapeutic response for a particular patient, composition, and mode of administration, without being toxic to the patient.

The selected dosage level will depend upon a variety of factors including the activity of the particular antibody, the clearance rate of the antibody, the duration of the treatment, other drugs, compounds and/or materials used in combination with the particular antibody, the age, sex, weight, condition, general health and prior medical history of the patient being treated, and like factors well known in the medical arts.

A physician or veterinarian having ordinary skill in the art can readily determine and prescribe the effective amount of the antibody composition required. For example, the physician or veterinarian could start doses of the antibody compositions at levels lower than that required to achieve the desired therapeutic effect and then gradually increasing the dosage until the desired effect is achieved.

In some embodiments, an antibody composition of the invention is provided to a subject chronically. Chronic treatments include any form of repeated administration for an extended period of time, such as repeated administrations for one or more months, between a month and a year, one or more years, or longer. In some embodiments, a chronic treatment involves administering antibody compositions of the invention repeatedly over the life of the subject. In certain embodiments, chronic treatments involve regular administrations, for example one or more times a day, one or more times a week, or one or more times a month. In general, a suitable dose such as a daily dose of antibody compositions of the invention will be that amount that is the lowest dose effective to produce a therapeutic effect. Such an effective dose will generally depend upon the factors described above. In some embodiments, at least 0.5-1 mg/kg may be used. However, higher or lower amounts may be used. In some embodiments, an effective dose of an antibody described herein may be about 100 mg/kg or more. In some embodiments, 300 to 600 mg/kg may be used.

Neutralizing antibody preparations may be formulated for administration in any convenient way for use in human or veterinary medicine, by analogy with other antibodies. In some embodiments, aspects of the invention also relate to a method of making a medicament for use in treating a subject, e.g., for treating or preventing a JVC infection, or for inhibiting JCV replication or proliferation. Such preparations can be used for prophylactic treatment of a subject at risk for or suspected of having a JCV infection or being at risk for PML (e.g., for treatment of a subject prior to, during, and/or after the subject receives an immunomodulatory therapy). Accordingly, one or more antibody compositions described herein that modulate DNA virus replication or proliferation as described herein may be used for the preparation of a medicament for use in any of the methods of treatment described herein. In some embodiments, the invention provides for the use of one or more antibody compositions of the invention (e.g., identified as inhibiting JCV replication) for the manufacture of a medicament or pharmaceutical for treating a mammal (e.g., a human) having one or more symptoms of, or at risk for, JCV infection, replication and/or proliferation (e.g., one or more symptoms of JCV activity). Accordingly, aspects of the invention relate to the use of one or more antibody compositions described herein for the preparation of a medicament for treating or preventing PML in a subject. Accordingly, the invention also relates to one or more antibody compositions described herein for use as a medicament. The invention also relates to one or more of these antibody compositions for use in methods described herein, for example in methods of inhibiting JCV replication, or of treating or preventing a disease associated with JCV replication or proliferation (e.g., in subjects that are about to be, are being, and/or have been treated with at least one immunomodulatory composition).

Diagnostic Applications and Kits:

In some embodiments, antibodies described herein can be used as detection reagents for in vivo diagnostics, and/or coupled to contrast dye reagents for radiology.

In some embodiments, aspects of the invention include using immobilized or non-immobilized, anti-JCV antibodies (e.g., VP-1 binding antibodies) as detection moieties to assess the presence and/or level of JCV in a sample. Detection assays may include the use of one or more labeled detection moieties (e.g., a VP-1 binding antibody containing or attached to a detectable label). A detectable label is defined as any moiety that can be detected using an assay. The antibodies and functional antibody fragments of the invention can be coupled to specific labeling agents for detecting binding according to standard coupling procedures. A wide variety of detectable labels can be used, such as those that provide direct detection (e.g., a radioactive label, a fluorophore, [e.g. Green Fluorescent Protein (GFP), Red Fluorescent Protein (RFP), etc.], a chromophore, an optical or electron dense label, etc.) or indirect detection (e.g., an enzyme tag such as horseradish peroxidase, etc.). Non-limiting examples of detectable labels that have been attached to or incorporated into antibodies include: enzymes, radiolabels, fluorescent labels, phosphorescent molecules, chemiluminescent molecules, chromophores, luminescent molecules, photoaffinity molecules, and colored particles or ligands such as biotin, etc. In some embodiments, detection methods of the invention may include electrochemiluminescence methods (ECL).

A variety of methods may be used to detect a label, depending on the nature of the label and other assay components. Labels may be directly detected through optical or electron density, radioactive emissions, non-radiative energy transfers, etc. or indirectly detected with antibody conjugates, streptavidin-biotin conjugates, etc. Many additional detectable labels are known in the art, as are methods for their attachment to antibodies.

Labeled antibodies of the invention may be antibodies that are used in vitro, e.g., in an immunoassay such as an ELISA. Such detectably labeled antibodies may be antibodies that have a detectable label incorporated into the antibody or may be antibodies that are linked to a secondary binding ligand and/or to an enzyme (an enzyme tag) that will generate a detectable (e.g., colored) product upon contact with a chromogenic substrate. Examples of suitable enzymes include, but are not limited to, urease, alkaline phosphatase, (horseradish) hydrogen peroxidase or glucose oxidase. Examples of suitable secondary binding ligands include, but are not limited to, biotin and/or avidin and streptavidin compounds. The use of such labels is well known to those of skill in the art and is described, for example, in U.S. Pat. Nos. 3,817,837; 3,850,752; 3,939,350; 3,996,345; 4,277,437; 4,275,149 and 4,366,241; each incorporated herein by reference.

Numerous methods for the attachment or conjugation of an antibody to its detectable label are known in the art. An attachment method may include the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3alpha-6alpha-diphenylglycouril-3 attached to the antibody (see, for example, U.S. Pat. Nos. 4,472,509 and 4,938,948, each incorporated herein by reference). Monoclonal antibodies also can be reacted with an enzyme in the presence of a coupling agent such as glutaraldehyde or periodate. Antibodies may be labeled with fluorescein markers in the presence of these coupling agents or by reaction with an isothiocyanate. In other embodiments, antibodies may be labeled by derivatization, for example, by selectively introducing sulfhydryl groups in the Fc region of the antibody, using reaction conditions that do not alter the antibody recognition site.

Detection of a detectable label in an assay of the invention is also referred to herein as detecting the "signal". Methods for detecting the signal in an immunoassay are well known in the art. In some embodiments, an assay signal can be detected using a multi-well plate reader (e.g. microplate reader) to assess the amount and/or location of a signal. Signal detection can be optical detection or other detection means suitable for detecting a detectable label utilized in the invention.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1

Antibody and CDR Sequences

A panel of neutralizing monoclonal antibody candidates was generated in by standard immunization techniques in mice. After screening ~300 individual clones, 6 clones were selected as potential blocking antibodies. An additional antibody had been developed for its ability to preferentially recognize the JCV-VP1 S269F variant.

The antibodies were designated 14G8, 16H5, 8D6, 18C9, 32A5, and 34C6. The S269F specific binder, 1B1, has a preference for S269F but has some affinity to 5269 as well. Antibody 8D6 recognizes JCV VLPs with high affinity but is a poor neutralizer of infectivity. The sequences of the mouse antibodies 14G8, 16H5, 18C9, and 34C6 are listed below.

Antibodies 18C9, 16H5, 14G8 and 1B1 have predicted deamidation sites in the second CDR of their heavy chains. These sites were engineered out of the genes for antibody 18C9 with the following substitutions: Heavy Chain N55Q, N55S, N55D, N55H, N55T, N55A, N55L and G56A, G56V, G56P. The deamidation mutant N55H retained reactivity to all JC virus-like particles indicating no loss of binding. All other deamidation mutants resulted in some changes in binding to common PMLgenic VP1 variants Antibody 18C9 has a free cysteine in the third CDR of the light chain. This sites was engineered out of the genes for antibody 18C9 with the following substitutions: Light Chain—C96S, C96A, C96L. The free cysteine was successively removed by the C96S substitution.

In the experiments presented in the following examples, the mouse-monoclonal sequences were coupled with human Fc, resulting in a chimeric antibody. The Experiments were performed in antibodies without signal sequences (highlighted)

14G8 antibody

14G8 Heavy chain

SEQ ID NO: 1

MVDIPMGCSWVILFLLSGTAGVHSEVQLQQSGPELVKPGASMKISCKASGYSFTGYTMNWVKESHGKNLDWIGLI

NPYNGGTRYDQKFKGKATLTVDKSSTTAYMELLSLTSEDSAVYYCARSHHYASGDEYFDYWGQGTTLTVSS

-continued

14G8 Heavy chain no signal seq

SEQ ID NO: 2

EVQLQQSGPELVKPGASMKISCKASGYSFTGYTMNWVKESHGKNLDWIGLINPYNGGTRYDQKFKGKATLTVDKS

STTAYMELLSLTSEDSAVYYCARSHHYASGDEYFDYWGQGTTLTVSS

14G8 Light chain

SEQ ID NO: 3

MESHTWFVYMLLWLSGVEGDIVMTQSHKFMSTSVGDRVSITCKASQNVGTAVAWYQQKPGQSPKVLIYWASTRH

TGVPDRFTGSGSGTDFTLTISNVQSEDLADYFCQQYSSYPLTFGAGTKLELK

14G8 Light chain no signal seq

SEQ ID NO: 4

DIVMTQSHKFMSTSVGDRVSITCKASQNVGTAVAWYQQKPGQSPKVLIYWASTRHTGVPDRFTGSGSGTDFTLTI

SNVQSEDLADYFCQQYSSYPLTFGAGTKLELK

16H5 antibody

16H5 Heavy chain

SEQ ID NO: 5

MECSWVMLFLLSGTAGVHSEVHLQQSGPELVKPGASMKISCRTSGYSFTGYTMNWVKQTHGKILEWIGLINPYNG

GVTYNQKFKGKATLTVDKSSSTTYLELLSLTSEDSAVYYCARSHNYGTGDEYFDYWGQGTTLTVYS

16H5 Heavy chain no signal seq

SEQ ID NO: 6

EVHLQQSGPELVKPGASMKISCRTSGYSFTGYTMNWVKQTHGKILEWIGLINPYNGGVTYNQKFKGKATLTVDKS

SSTTYLELLSLTSEDSAVYYCARSHNYGTGDEYFDYWGQGTTLTVYS

16H5 Light chain

SEQ ID NO: 7

MESQTQVFIYMLLWLSGVEGDIVMTQSHKFMSTSLGDRVNITCKASLAVGTAVAWYQQKPGQSPKLLIYWASTRP

TGVPSRFTGSGSGTDFTLTISNVQSEDLTDFFCQQYSSYPLTFGAGTKLELK

16H5 Light chain no signal seq

SEQ ID NO: 8

DIVMTQSHKFMSTSLGDRVNITCKASLAVGTAVAWYQQKPGQSPKLLIYWASTRPTGVPSRFTGSGSGTDFTLTI

SNVQSEDLTDFFCQQYSSYPLTFGAGTKLELK

18C9 antibody (CDR sequences underlined)

18C9 Heavy chain

SEQ ID NO: 9

MLEWSWVILFLLSGTAGVHSEVQLQQSGPELVKPGASMKISCKASGYSFTGYTLTWVKQSHGKNLDWIGLINPYN

GGTRYNQKFKGKATLTVDKSSSTAYMELLSLTSEDSAVYYCARLGYYATGDEYFDYWGQGTTLTVSS

18C9 Heavy chain no signal seq

SEQ ID NO: 10

EVQLQQSGPELVKPGASMKISCKASGYSFTGYTLTWVKQSHGKNLDWIGLINPYNGGTRYNQKFKGKATLTVDKS

SSTAYMELLSLTSEDSAVYYCARLGYYATGDEYFDYWGQGTTLTVSS

18C9 Light chain

SEQ ID NO: 11

MKSHTQVFIYMLLWLSGVEGDIVMTQSHKFMSTSVGDRVSITCKASQDVGTAVAWYQQKPGQSPKLLIYWASTRH

TGVPDRFTGSRSGTDFTLTISNVQSEDLADYFCQQYSSYPCTFGGGAKLEIR

18C9 Light chain no signal seq

SEQ ID NO: 12

DIVMTQSHKFMSTSVGDRVSITCKASQDVGTAVAWYQQKPGQSPKLLIYWASTRHTGVPDRFTGSRSGTDFTLTI

SNVQSEDLADYFCQQYSSYPCTFGGGAKLEIR

34C6 antibody (CDR sequences are underlined)

34C6 Heavy chain

SEQ ID NO: 13

EVQLQQSGTVLARPGASVKMSCKASAYTFTRYWMHWVKQRPGQGLEWIGAIYPGNSDTTYNQKFKGKAKLTAVTS

TSTAYMELSSLTNEDSAVYYCTKKGVRYYALDYWGQGTSVTVSS

34C6 Light chain

SEQ ID NO: 14

METDTLLLWVLLLWVPGSTGDIVLTQSPASLAVSLGQRATISCRASESVDSYGNSFVHWYQQKPGQPPKLLIYRA

SNLESGIPARFSGSGSRTDFTLTINPVEADDVATYYCLQSNEDPMYTFGGGTKLEIK

34C6 Light chain no signal seq

SEQ ID NO: 15

DIVLTQSPASLAVSLGQRATISCRASESVDSYGNSFVHWYQQKPGQPPKLLIYRASNLESGIPARFSGSGSRTDF

TLTINPVEADDVATYYCLQSNEDPMYTFGGGTKLEIK

Modified 18C9 antibody sequences (CDR sequences underlined; mutation highlighted and underlined)

18C9 Heavy chain, N55S:

SEQ ID NO: 16

MDFGLSLVFLVLILKGVQCEVQLQQSGPELVKPGASMKISCKASGYSFTGYTLTWVKQSHGKNLDWIGLINPYSG

GTRYNQKFKGKATLTVDKSSSTAYMELLSLTSEDSAVYYCARLGYYATGDEYFDYWGQGTTLTVSS

18C9 Heavy chain, N55S: no signal seq

SEQ ID NO: 17

EVQLQQSGPELVKPGASMKISCKASGYSFTGYTLTWVKQSHGKNLDWIGLINPYSGGTRYNQKFKGKATLTVDKS

SSTAYMELLSLTSEDSAVYYCARLGYYATGDEYFDYWGQGTTLTVSS

18C9 Heavy chain, N55Q:

SEQ ID NO: 18

MDFGLSLVFLVLILKGVQCEVQLQQSGPELVKPGASMKISCKASGYSFTGYTLTWVKQSHGKNLDWIGLINPYQG

GTRYNQKFKGKATLTVDKSSSTAYMELLSLTSEDSAVYYCARLGYYATGDEYFDYWGQGTTLTVSS

18C9 Heavy chain, N55Q: no signal seq

SEQ ID NO: 19

EVQLQQSGPELVKPGASMKISCKASGYSFTGYTLTWVKQSHGKNLDWIGLINPYQGGTRYNQKFKGKATLTVDKS

SSTAYMELLSLTSEDSAVYYCARLGYYATGDEYFDYWGQGTTLTVSS

18C9 Heavy chain, N55D:

SEQ ID NO: 20

MDFGLSLVFLVLILKGVQCEVQLQQSGPELVKPGASMKISCKASGYSFTGYTLTWVKQSHGKNLDWIGLINPYDG

GTRYNQKFKGKATLTVDKSSSTAYMELLSLTSEDSAVYYCARLGYYATGDEYFDYWGQGTTLTVSS

18C9 Heavy chain, N55D: no signal seq

SEQ ID NO: 21

EVQLQQSGPELVKPGASMKISCKASGYSFTGYTLTWVKQSHGKNLDWIGLINPYDGGTRYNQKFKGKATLTVDKS

SSTAYMELLSLTSEDSAVYYCARLGYYATGDEYFDYWGQGTTLTVSS

18C9 Heavy chain, N55H:

SEQ ID NO: 22

MDFGLSLVFLVLILKGVQCEVQLQQSGPELVKPGASMKISCKASGYSFTGYTLTWVKQSHGKNLDWIGLINPYHG

GTRYNQKFKGKATLTVDKSSSTAYMELLSLTSEDSAVYYCARLGYYATGDEYFDYWGQGTTLTVSS

18C9 Heavy chain, N55H: no signal seq

SEQ ID NO: 23

EVQLQQSGPELVKPGASMKISCKASGYSFTGYTLTWVKQSHGKNLDWIGLINPYHGGTRYNQKFKGKATLTVDKS

SSTAYMELLSLTSEDSAVYYCARLGYYATGDEYFDYWGQGTTLTVSS

18C9 Heavy chain, N55T:

SEQ ID NO: 24

MDFGLSLVFLVLILKGVQCEVQLQQSGPELVKPGASMKISCKASGYSFTGYTLTWVKQSHGKNLDWIGLINPYTG

GTRYNQKFKGKATLTVDKSSSTAYMELLSLTSEDSAVYYCARLGYYATGDEYFDYWGQGTTLTVSS

18C9 Heavy chain, N55T: no signal seq

SEQ ID NO: 25

EVQLQQSGPELVKPGASMKISCKASGYSFTGYTLTWVKQSHGKNLDWIGLINPYTGGTRYNQKFKGKATLTVDKS

SSTAYMELLSLTSEDSAVYYCARLGYYATGDEYFDYWGQGTTLTVSS

-continued

18C9 Heavy chain, N55A:
SEQ ID NO: 26

MDFGLSLVFLVLILKGVQCEVQLQQSGPELVKPGASMKISCKASGYSFTGYTLTWVKQSHGKNLDWIGLINPYAG
GTRYNQKFKGKATLTVDKSSTAYMELLSLTSEDSAVYYCARLGYYATGDEYFDYWGQGTTLTVSS

18C9 Heavy chain, N55A: no signal seq
SEQ ID NO: 27

EVQLQQSGPELVKPGASMKISCKASGYSFTGYTLTWVKQSHGKNLDWIGLINPYAGGTRYNQKFKGKATLTVDKS
SSTAYMELLSLTSEDSAVYYCARLGYYATGDEYFDYWGQGTTLTVSS

18C9 Heavy chain, N55L:
SEQ ID NO: 28

MDFGLSLVFLVLILKGVQCEVQLQQSGPELVKPGASMKISCKASGYSFTGYTLTWVKQSHGKNLDWIGLINPYLG
GTRYNQKFKGKATLTVDKSSTAYMELLSLTSEDSAVYYCARLGYYATGDEYFDYWGQGTTLTVSS

18C9 Heavy chain, N55L: no signal seq
SEQ ID NO: 29

EVQLQQSGPELVKPGASMKISCKASGYSFTGYTLTWVKQSHGKNLDWIGLINPYLGGTRYNQKFKGKATLTVDKS
SSTAYMELLSLTSEDSAVYYCARLGYYATGDEYFDYWGQGTTLTVSS

18C9 Heavy chain, N55X:
SEQ ID NO: 30

MDFGLSLVFLVLILKGVQCEVQLQQSGPELVKPGASMKISCKASGYSFTGYTLTWVKQSHGKNLDWIGLINPYXG
GTRYNQKFKGKATLTVDKSSTAYMELLSLTSEDSAVYYCARLGYYATGDEYFDYWGQGTTLTVSS

18C9 Heavy chain, N55X: no signal seq
SEQ ID NO: 31

EVQLQQSGPELVKPGASMKISCKASGYSFTGYTLTWVKQSHGKNLDWIGLINPYXGGTRYNQKFKGKATLTVDKS
SSTAYMELLSLTSEDSAVYYCARLGYYATGDEYFDYWGQGTTLTVSS

18C9 Heavy chain, G56A:
SEQ ID NO: 32

MDFGLSLVFLVLILKGVQCEVQLQQSGPELVKPGASMKISCKASGYSFTGYTLTWVKQSHGKNLDWIGLINPYNA
GTRYNQKFKGKATLTVDKSSTAYMELLSLTSEDSAVYYCARLGYYATGDEYFDYWGQGTTLTVSS

18C9 Heavy chain, G56A: no signal seq
SEQ ID NO: 33

EVQLQQSGPELVKPGASMKISCKASGYSFTGYTLTWVKQSHGKNLDWIGLINPYNAGTRYNQKFKGKATLTVDKS
SSTAYMELLSLTSEDSAVYYCARLGYYATGDEYFDYWGQGTTLTVSS

18C9 Heavy chain, G56V:
SEQ ID NO: 34

MDFGLSLVFLVLILKGVQCEVQLQQSGPELVKPGASMKISCKASGYSFTGYTLTWVKQSHGKNLDWIGLINPYNV
GTRYNQKFKGKATLTVDKSSTAYMELLSLTSEDSAVYYCARLGYYATGDEYFDYWGQGTTLTVSS

18C9 Heavy chain, G56V: no signal seq
SEQ ID NO: 35

EVQLQQSGPELVKPGASMKISCKASGYSFTGYTLTWVKQSHGKNLDWIGLINPYNVGTRYNQKFKGKATLTVDKS
SSTAYMELLSLTSEDSAVYYCARLGYYATGDEYFDYWGQGTTLTVSS

18C9 Heavy chain, G56P:
SEQ ID NO: 36

MDFGLSLVFLVLILKGVQCEVQLQQSGPELVKPGASMKISCKASGYSFTGYTLTWVKQSHGKNLDWIGLINPYNP
GTRYNQKFKGKATLTVDKSSTAYMELLSLTSEDSAVYYCARLGYYATGDEYFDYWGQGTTLTVSS

18C9 Heavy chain, G56P: no signal seq
SEQ ID NO: 37

EVQLQQSGPELVKPGASMKISCKASGYSFTGYTLTWVKQSHGKNLDWIGLINPYNPGTRYNQKFKGKATLTVDKS
SSTAYMELLSLTSEDSAVYYCARLGYYATGDEYFDYWGQGTTLTVSS

18C9 Heavy, G56X:

SEQ ID NO: 38

MDFGLSLVFLVLILKGVQCEVQLQQSGPELVKPGASMKISCKASGYSFTGYTLTWVKQSHGKNLDWIGLINPYNX
GTRYNQKFKGKATLTVDKSSSTAYMELLSLTSEDSAVYYCARLGYYATGDEYFDYWGQGTTLTVSS

18C9 Heavy chain, G56X: no signal seq

SEQ ID NO: 39

EVQLQQSGPELVKPGASMKISCKASGYSFTGYTLTWVKQSHGKNLDWIGLINPYNXGTRYNQKFKGKATLTVDKS
SSTAYMELLSLTSEDSAVYYCARLGYYATGDEYFDYWGQGTTLTVSS

18C9 Light chain C96L:

SEQ ID NO: 40

MRVPAQLLGLLLWLPGARCDIVMTQSHKEMSTSVGDRVSITCKASQDVGTAVAWYQQKPGQSPKLLIYWASTRH
TGVPDRFTGSRSGTDFTLTISNVQSEDLADYFCQQYSSYPLTFGGGAKLEIR

18C9 Light chain C96L: no signal seq

SEQ ID NO: 41

DIVMTQSHKFMSTSVGDRVSITCKASQDVGTAVAWYQQKPGQSPKLLIYWASTRHTGVPDRFTGSRSGTDFTLTI
SNVQSEDLADYFCQQYSSYPLTFGGGAKLEIR

18C9 Light chain C96S:

SEQ ID NO: 42

MRVPAQLLGLLLLWLPGARCDIVMTQSHKEMSTSVGDRVSITCKASQDVGTAVAWYQQKPGQSPKLLIYWASTRH
TGVPDRFTGSRSGTDFTLTISNVQSEDLADYFCQQYSSYPSTFGGGAKLEIR

18C9 Light chain C96S: no signal seq

SEQ ID NO: 43

DIVMTQSHKFMSTSVGDRVSITCKASQDVGTAVAWYQQKPGQSPKLLIYWASTRHTGVPDRFTGSRSGTDFTLTI
SNVQSEDLADYFCQQYSSYPSTFGGGAKLEIR

18C9 Light chain C96A:

SEQ ID NO: 44

MRVPAQLLGLLLWLPGARCDIVMTQSHKFMSTSVGDRVSITCKASQDVGTAVAWYQQKPGQSPKLLIYWASTRH
TGVPDRFTGSRSGTDFTLTISNVQSEDLADYFCQQYSSYPATFGGGAKLEIR

18C9 Light chain C96A: no signal seq

SEQ ID NO: 45

DIVMTQSHKFMSTSVGDRVSITCKASQDVGTAVAWYQQKPGQSPKLLIYWASTRHTGVPDRFTGSRSGTDFTLTI
SNVQSEDLADYFCQQYSSYPATFGGGAKLEIR

18C9 Light chain, C96X:

SEQ ID NO: 46

MRVPAQLLGLLLAWLPGARCDIVMTQSHKFMSTSVGDRVSITCKASQDVGTAVAWYQQKPGQSPKLLIYWASTRH
TGVPDRFTGSRSGTDFTLTISNVQSEDLADYFCQQYSSYPXTFGGGAKLEIR

18C9 Light chain, C96X: no signal seq

SEQ ID NO: 47

DIVMTQSHKFMSTSVGDRVSITCKASQDVGTAVAWYQQKPGQSPKLLIYWASTRHTGVPDRFTGSRSGTDFTLTI
SNVQSEDLADYFCQQYSSYPXTFGGGAKLEIR

| 18C9 CDR sequences |
|---| heavy chain CDR1

SEQ ID NO: 48

GYTLT heavy chain CDR2

SEQ ID NO: 49

LINPYNGGTRYNQKFKG heavy chain CDR2 N55S

SEQ ID NO: 50

LINPYSGGTRYNQKFKG

| | |
|---|---|
| heavy chain CDR2 N55Q<br>LINPYQGGTRYNQKFKG | SEQ ID NO: 51 |
| heavy chain CDR2 N55D<br>LINPYDGGTRYNQKFKG | SEQ ID NO: 52 |
| heavy chain CDR2 N55H<br>LINPYHGGTRYNQKFKG | SEQ ID NO: 53 |
| heavy chain CDR2 N55T<br>LINPYTGGTRYNQKFKG | SEQ ID NO: 54 |
| heavy chain CDR2 N55A<br>LINPYAGGTRYNQKFKG | SEQ ID NO: 55 |
| heavy chain CDR2 N55L<br>LINPYLGGTRYNQKFKG | SEQ ID NO: 56 |
| heavy chain CDR2 N55X<br>LINPYXGGTRYNQKFKG | SEQ ID NO: 57 |
| heavy chain CDR2 G56A<br>LINPYNAGTRYNQKFKG | SEQ ID NO: 58 |
| heavy chain CDR2 G56V<br>LINPYNVGTRYNQKFKG | SEQ ID NO: 59 |
| heavy chain CDR2 G56P<br>LINPYNPGTRYNQKFKG | SEQ ID NO: 60 |
| heavy chain CDR2 G56X<br>LINPYNXGTRYNQKFKG | SEQ ID NO: 61 |
| heavy chain CDR2 N55X G56X<br>LINPYXXGTRYNQKFKG | SEQ ID NO: 62 |
| heavy chain CDR3<br>LGYYATGDEYFDY | SEQ ID NO: 63 |
| light chain CDR1<br>KASQDVGTAVA | SEQ ID NO: 64 |
| light chain CDR2<br>WASTRHT | SEQ ID NO: 65 |
| light chain CDR3<br>QQYSSYPCT | SEQ ID NO: 66 |
| light chain CDR3 C96L<br>QQYSSYPLT | SEQ ID NO: 67 |
| light chain CDR3 C96S<br>QQYSSYPST | SEQ ID NO: 68 |
| light chain CDR3 C96A<br>QQYSSYPAT | SEQ ID NO: 69 |

-continued light chain CDR3 C96X

SEQ ID NO: 70

QQYSSYPXT

Example 2

Binding to JCV-VP1 of CH-P18C9 Antibody (=Chimeric 18C9 Including SEQ ID NO:10 and SEQ ID NO:12) as Determined by ELISA The binding of CH-P18C9 antibody (=chimeric 18C9 including SEQ ID NO:11 and SEQ ID NO:12) to a number of wild-type and mutant JCV-VP1 was evaluated using ELISA. The results are summarized in FIG. 1.

Example 3

Binding to JCV-VP1 of CH-P18C9 Antibody (=Chimeric 18C9 Including SEQ ID NO:10 and SEQ ID NO:12) as Determined by Biacore The binding of CH-P18C9 antibody (=chimeric 18C9 including SEQ ID NO:10 and SEQ ID NO:12) to a number of wild-type and mutant JCV-VP1 was evaluated using Biacore. The results are summarized in FIG. 2.

Example 4

Infectivity Assay with Mutant JCV-VP1 Viruses

Figure 6:
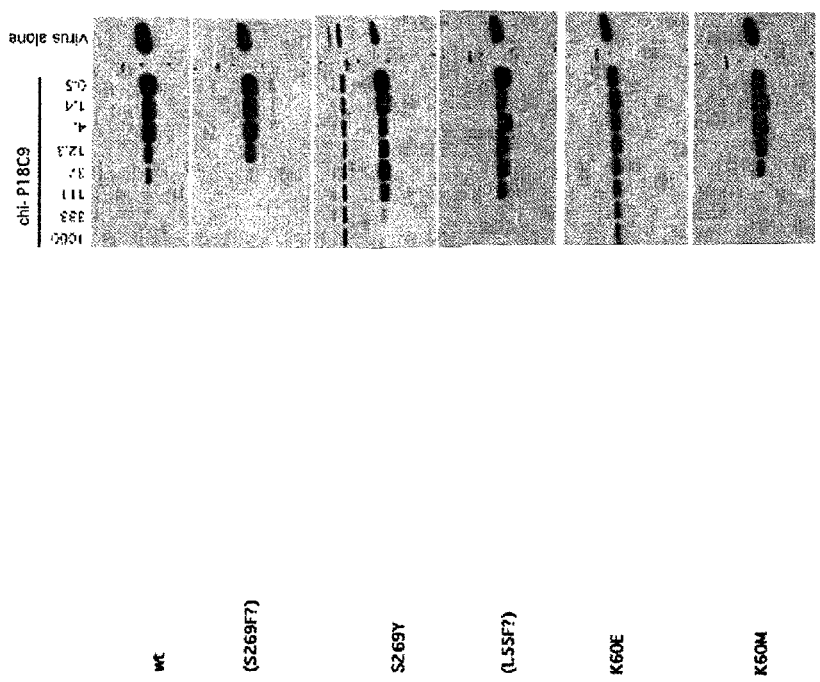
FIG. 6 shows the results of the viral mutant infectivity assay as shown by Western blot.
Figure 8:
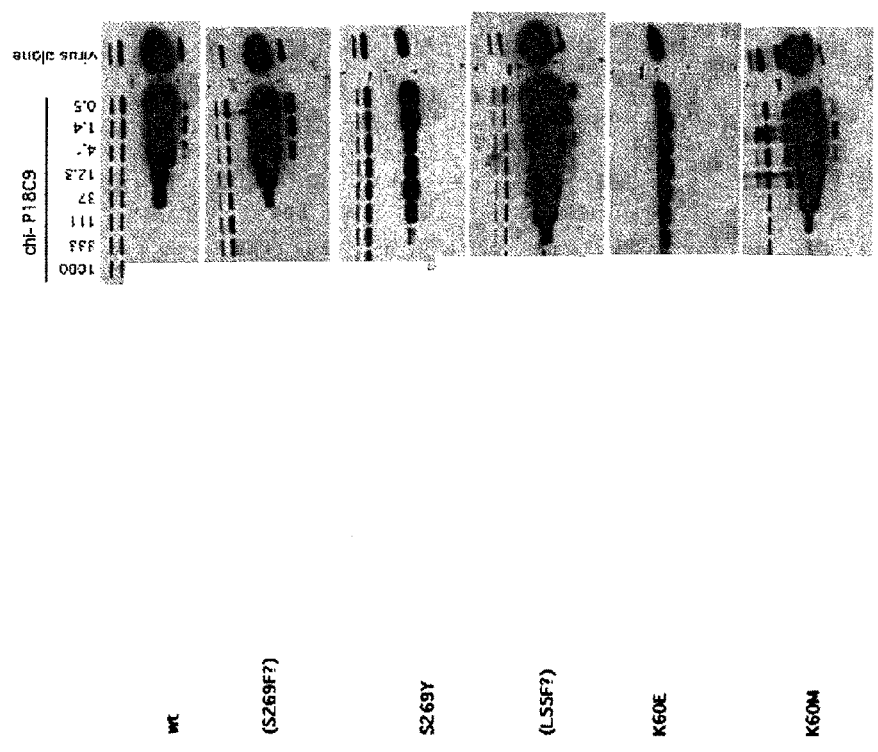
FIG. 8 shows the results of the viral mutant infectivity assay as shown by Western blot.

The ability of antibody chi-18C9 (=chimeric 18C9 including SEQ ID NO:10 and SEQ ID NO:12) to suppress the infectivity of the JCV-VP1 mutants was evaluated. The assay conditions are provided in FIG. 4 and FIG. 5. The read-out of the experiments was done by Western-Blots. The results of the Western blots are shown in FIGS. 6-7 (regular exposure) and FIGS. 8-9 (over-exposure).

Example 5

Generation of Deamidation Mutants of Antibody 18C9

An overview of the generation of the deamidation mutants of antibody 18C9 is provided in FIG. 10. The purification of the mutants is summarized in FIG. 11.

Example 6

Binding of Deamidation Mutants of Antibody 18C9 to Mutant JCV-VP1 Viruses

Figure 12:
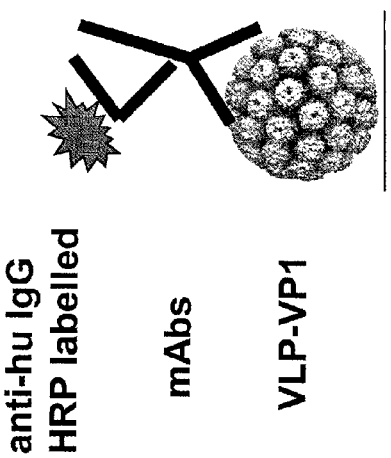
FIG. 12 shows an overview of a JCV-VLP1 binding ELISA assay.
Figure 13:
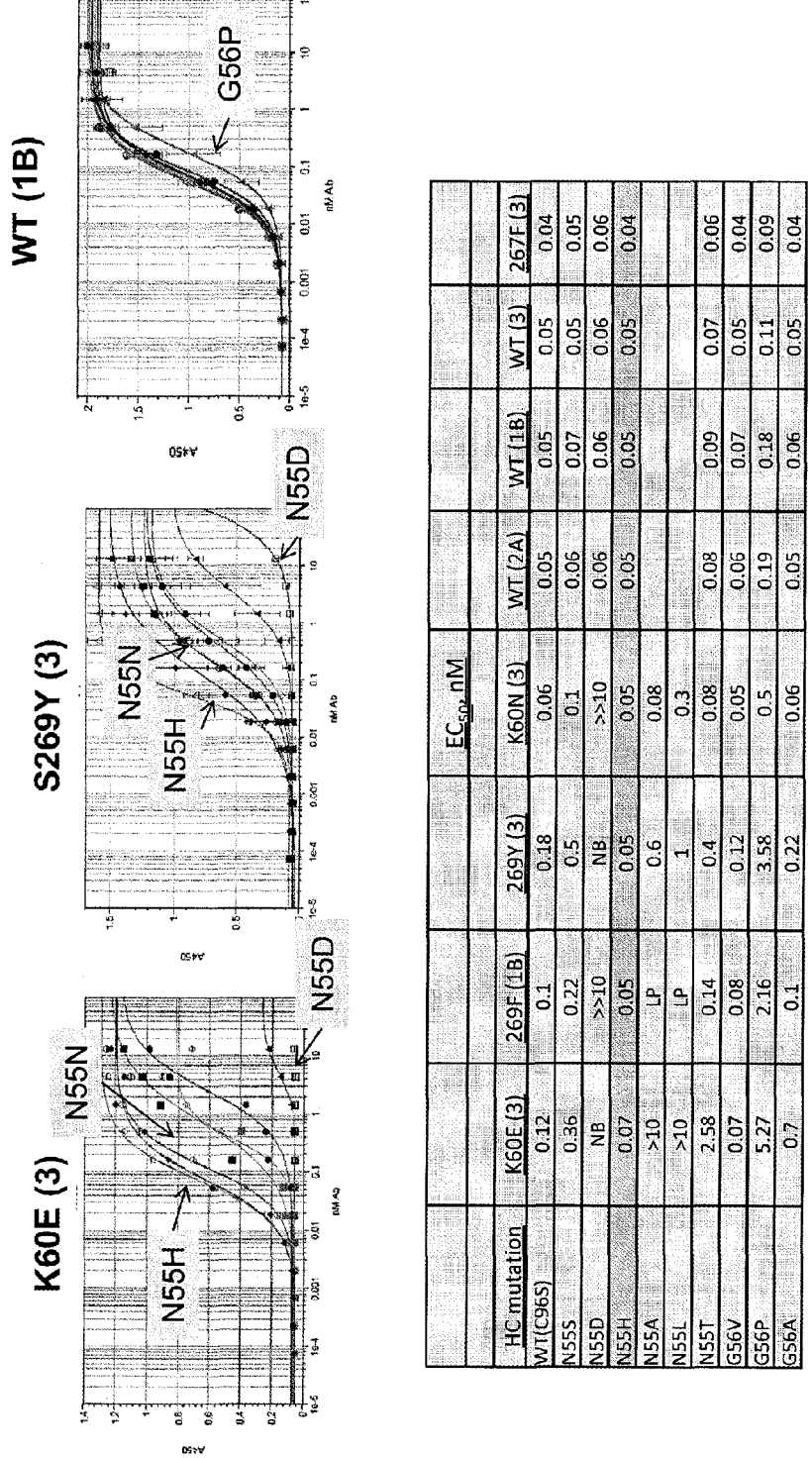
FIG. 13 shows an overview of results of a JCV-VLP1 binding ELISA assay.

The ability of deamidation mutants of antibody 18C9 to bind the various JCV-VP1 mutants was evaluated by ELISA. An overview of the ELISA assay is provided in FIG. 12. The ELISA result of the binding of the deamidation mutants of antibody 18C9 to JCV-VP1 WT and various JCV-VP1 mutants is provided in FIG. 13. Conditions of an additional assay are provided in FIG. 14. The $EC_{50}$ values (in nM) are provided in FIG. 15.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety, particularly for the use or subject matter referenced herein.

What is claimed is:

1. An isolated monoclonal antibody comprising:
a heavy chain variable domain comprising a CDR1 amino acid sequence that is identical to the amino acid sequence of SEQ ID NO:48, a CDR2 amino acid sequence that is identical to the amino acid sequence of SEQ ID NO:49, and a CDR3 amino acid sequence that is identical to the amino acid sequence of SEQ ID NO:63; and
a light chain variable domain comprising a CDR1 amino acid sequence that is identical to the amino acid sequence of SEQ ID NO:64, a CDR2 amino acid sequence that is identical to the amino acid sequence of SEQ ID NO:65, and a CDR3 amino acid sequence that is identical to the amino acid sequence of SEQ ID NO:66).

2. The isolated monoclonal antibody of claim 1, wherein at least one framework region amino acid sequence of the heavy chain variable domain is at least 90% identical to at least one corresponding framework region amino acid sequence of a heavy chain variable domain amino acid sequence that is identical to the amino acid sequence of SEQ ID NO:10.

3. The isolated monoclonal antibody of claim 1, wherein the isolated monoclonal antibody comprises a heavy chain variable domain amino acid sequence that is at least 90% identical to the amino acid sequence of SEQ ID NO:10.

4. The isolated monoclonal antibody of claim 3, wherein the isolated monoclonal antibody comprises a heavy chain variable domain amino acid sequence that is identical to the amino acid sequence of SEQ ID NO:10.

5. The isolated monoclonal antibody of claim 1, wherein at least one framework region amino acid sequence of the light chain variable domain is at least 90% identical to at least one corresponding framework region amino acid sequence of a light chain variable domain amino acid sequence that is identical to the amino acid sequence of SEQ ID NO:12.

6. The isolated monoclonal antibody of claim 1, wherein the isolated monoclonal antibody comprises a light chain variable domain amino acid sequence that is at least 90% identical to the amino acid sequence of SEQ ID NO:12.

7. The isolated monoclonal antibody of claim 6, wherein the isolated monoclonal antibody comprises a light chain variable domain amino acid sequence that is identical to the amino acid sequence of SEQ ID NO:12.

8. The isolated monoclonal antibody of claim 1, wherein the isolated monoclonal antibody comprises a heavy chain variable domain amino acid sequence that is identical to the amino acid sequence of SEQ ID NO:10 and a light chain variable domain amino acid sequence that is identical to the amino acid sequence of SEQ ID NO:12.

9. The isolated monoclonal antibody of claim 1, wherein the isolated monoclonal antibody is an isolated chimeric monoclonal antibody.

10. The isolated monoclonal antibody of claim 1, wherein the isolated monoclonal antibody comprises an IgG1 Fc-region.

11. The isolated monoclonal antibody of claim 8, wherein the isolated monoclonal antibody is an isolated chimeric monoclonal antibody.

12. The isolated monoclonal antibody of claim 8, wherein the isolated monoclonal antibody comprises an IgG1 Fc-region.

13. An isolated monoclonal antibody comprising:
a heavy chain variable domain comprising a CDR1 amino acid sequence that is identical to the amino acid sequence of SEQ ID NO:48, a CDR2 amino acid sequence that is identical to the amino acid sequence of SEQ ID NO:53, and a CDR3 amino acid sequence that is identical to the amino acid sequence of SEQ ID NO:63; and
a light chain variable domain comprising a CDR1 amino acid sequence that is identical to the amino acid sequence of SEQ ID NO:64, a CDR2 amino acid sequence that is identical to the amino acid sequence of SEQ ID NO:65, and a CDR3 amino acid sequence that is identical to the amino acid sequence of SEQ ID NO:68).

14. The isolated monoclonal antibody of claim 13, wherein at least one framework region amino acid sequence of the heavy chain variable domain is at least 90% identical to at least one corresponding framework region amino acid sequence of a heavy chain variable domain amino acid sequence that is identical to the amino acid sequence of SEQ ID NO:23.

15. The isolated monoclonal antibody of claim 13, wherein the isolated monoclonal antibody comprises a heavy chain variable domain amino acid sequence that is at least 90% identical to the amino acid sequence of SEQ ID NO:23.

16. The isolated monoclonal antibody of claim 15, wherein the isolated monoclonal antibody comprises a heavy chain variable domain amino acid sequence that is identical to the amino acid sequence of SEQ ID NO:23.

17. The isolated monoclonal antibody of claim 13, wherein at least one framework region amino acid sequence of the light chain variable domain is at least 90% identical to at least one corresponding framework region amino acid sequence of a light chain variable domain amino acid sequence that is identical to the amino acid sequence of SEQ ID NO:43.

18. The isolated monoclonal antibody of claim 13, wherein the isolated monoclonal antibody comprises a light chain variable domain amino acid sequence that is at least 90% identical to the amino acid sequence of SEQ ID NO:43.

19. The isolated monoclonal antibody of claim 18, wherein the isolated monoclonal antibody comprises a light chain variable domain amino acid sequence that is identical to the amino acid sequence of SEQ ID NO:43.

20. The isolated monoclonal antibody of claim 13, wherein the isolated monoclonal antibody comprises a heavy chain variable domain amino acid sequence that is identical to the amino acid sequence of SEQ ID NO:23 and a light chain variable domain amino acid sequence that is identical to the amino acid sequence of SEQ ID NO:43.

21. The isolated monoclonal antibody of claim 13, wherein the isolated monoclonal antibody is an isolated chimeric monoclonal antibody.

22. The isolated monoclonal antibody of claim 13, wherein the isolated monoclonal antibody comprises an IgG1 Fc-region.

23. The isolated monoclonal antibody of claim 20, wherein the isolated monoclonal antibody is an isolated chimeric monoclonal antibody.

24. The isolated monoclonal antibody of claim 20, wherein the isolated monoclonal antibody comprises an IgG1 Fc-region.

* * * * *

SEQUENCE LISTING

```
<160> NUMBER OF SEQ ID NOS: 74

<210> SEQ ID NO 1
<211> LENGTH: 146
<212> TYPE: PRT
<213> ORGANISM: Artificial Sequence
<220> FEATURE:
<223> OTHER INFORMATION: Synthetic Polypeptide

<400> SEQUENCE: 1

Met Val Asp Ile Pro Met Gly Cys Ser Trp Val Ile Leu Phe Leu Leu
1               5                   10                  15

Ser Gly Thr Ala Gly Val His Ser Glu Val Gln Leu Gln Gln Ser Gly
            20                  25                  30

Pro Glu Leu Val Lys Pro Gly Ala Ser Met Lys Ile Ser Cys Lys Ala
        35                  40                  45
```

```
Ser Gly Tyr Ser Phe Thr Gly Tyr Thr Met Asn Trp Val Lys Glu Ser
    50                  55                  60

His Gly Lys Asn Leu Asp Trp Ile Gly Leu Ile Asn Pro Tyr Asn Gly
 65                  70                  75                  80

Gly Thr Arg Tyr Asp Gln Lys Phe Lys Gly Lys Ala Thr Leu Thr Val
                85                  90                  95

Asp Lys Ser Ser Thr Thr Ala Tyr Met Glu Leu Leu Ser Leu Thr Ser
                100                 105                 110

Glu Asp Ser Ala Val Tyr Tyr Cys Ala Arg Ser His His Tyr Ala Ser
                115                 120                 125

Gly Asp Glu Tyr Phe Asp Tyr Trp Gly Gln Gly Thr Thr Leu Thr Val
    130                 135                 140

Ser Ser
145

<210> SEQ ID NO 2
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 2

Glu Val Gln Leu Gln Gln Ser Gly Pro Glu Leu Val Lys Pro Gly Ala
 1               5                  10                  15

Ser Met Lys Ile Ser Cys Lys Ala Ser Gly Tyr Ser Phe Thr Gly Tyr
                20                  25                  30

Thr Met Asn Trp Val Lys Glu Ser His Gly Lys Asn Leu Asp Trp Ile
            35                  40                  45

Gly Leu Ile Asn Pro Tyr Asn Gly Gly Thr Arg Tyr Asp Gln Lys Phe
 50                  55                  60

Lys Gly Lys Ala Thr Leu Thr Val Asp Lys Ser Ser Thr Thr Ala Tyr
 65                  70                  75                  80

Met Glu Leu Leu Ser Leu Thr Ser Glu Asp Ser Ala Val Tyr Tyr Cys
                85                  90                  95

Ala Arg Ser His His Tyr Ala Ser Gly Asp Glu Tyr Phe Asp Tyr Trp
                100                 105                 110

Gly Gln Gly Thr Thr Leu Thr Val Ser Ser
            115                 120

<210> SEQ ID NO 3
<211> LENGTH: 127
<212> TYPE: PRT
<213> ORGANISM: Artificial Sequence
<220> FEATURE:
<223> OTHER INFORMATION: Synthetic Polypeptide

<400> SEQUENCE: 3

Met Glu Ser His Thr Gln Val Phe Val Tyr Met Leu Leu Trp Leu Ser
 1               5                  10                  15

Gly Val Glu Gly Asp Ile Val Met Thr Gln Ser His Lys Phe Met Ser
                20                  25                  30

Thr Ser Val Gly Asp Arg Val Ser Ile Thr Cys Lys Ala Ser Gln Asn
            35                  40                  45

Val Gly Thr Ala Val Ala Trp Tyr Gln Gln Lys Pro Gly Gln Ser Pro
 50                  55                  60

Lys Val Leu Ile Tyr Trp Ala Ser Thr Arg His Thr Gly Val Pro Asp
 65                  70                  75                  80
```

```
Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Tyr Pro Leu Thr Phe Gly Ala Gly Thr Lys Leu Glu Leu Lys
        115                 120                 125

<210> SEQ ID NO 4
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 4

Asp Ile Val Met Thr Gln Ser His Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Val Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105

<210> SEQ ID NO 5
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 5

Met Glu Cys Ser Trp Val Met Leu Phe Leu Leu Ser Gly Thr Ala Gly
1               5                   10                  15

Val His Ser Glu Val His Leu Gln Gln Ser Gly Pro Glu Leu Val Lys
            20                  25                  30

Pro Gly Ala Ser Met Lys Ile Ser Cys Arg Thr Ser Gly Tyr Ser Phe
        35                  40                  45

Thr Gly Tyr Thr Met Asn Trp Val Lys Gln Thr His Gly Lys Ile Leu
    50                  55                  60

Glu Trp Ile Gly Leu Ile Asn Pro Tyr Asn Gly Val Thr Tyr Asn
65                  70                  75                  80

Gln Lys Phe Lys Gly Lys Ala Thr Leu Thr Val Asp Lys Ser Ser Ser
                85                  90                  95

Thr Thr Tyr Leu Glu Leu Leu Ser Leu Thr Ser Glu Asp Ser Ala Val
            100                 105                 110

Tyr Tyr Cys Ala Arg Ser His Asn Tyr Gly Thr Gly Asp Glu Tyr Phe
        115                 120                 125

Asp Tyr Trp Gly Gln Gly Thr Thr Leu Thr Val Tyr Ser
    130                 135                 140
```

-continued

```
<210> SEQ ID NO 6
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 6

Glu Val His Leu Gln Gln Ser Gly Pro Glu Leu Val Lys Pro Gly Ala
1               5                   10                  15

Ser Met Lys Ile Ser Cys Arg Thr Ser Gly Tyr Ser Phe Thr Gly Tyr
            20                  25                  30

Thr Met Asn Trp Val Lys Gln Thr His Gly Lys Ile Leu Glu Trp Ile
        35                  40                  45

Gly Leu Ile Asn Pro Tyr Asn Gly Gly Val Tyr Asn Gln Lys Phe
    50                  55                  60

Lys Gly Lys Ala Thr Leu Thr Val Asp Lys Ser Ser Ser Thr Thr Tyr
65                  70                  75                  80

Leu Glu Leu Leu Ser Leu Thr Ser Glu Asp Ser Ala Val Tyr Tyr Cys
                85                  90                  95

Ala Arg Ser His Asn Tyr Gly Thr Gly Asp Glu Tyr Phe Asp Tyr Trp
            100                 105                 110

Gly Gln Gly Thr Thr Leu Thr Val Tyr Ser
        115                 120

<210> SEQ ID NO 7
<211> LENGTH: 127
<212> TYPE: PRT
<213> ORGANISM: Artificial Sequence
<220> FEATURE:
<223> OTHER INFORMATION: Synthetic Polypeptide

<400> SEQUENCE: 7

Met Glu Ser Gln Thr Gln Val Phe Ile Tyr Met Leu Leu Trp Leu Ser
1               5                   10                  15

Gly Val Glu Gly Asp Ile Val Met Thr Gln Ser His Lys Phe Met Ser
            20                  25                  30

Thr Ser Leu Gly Asp Arg Val Asn Ile Thr Cys Lys Ala Ser Leu Ala
        35                  40                  45

Val Gly Thr Ala Val Ala Trp Tyr Gln Gln Lys Pro Gly Gln Ser Pro
    50                  55                  60

Lys Leu Leu Ile Tyr Trp Ala Ser Thr Arg Pro Thr Gly Val Pro Ser
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Thr Asp Phe Phe Cys Gln Gln Tyr Ser
            100                 105                 110

Ser Tyr Pro Leu Thr Phe Gly Ala Gly Thr Lys Leu Glu Leu Lys
        115                 120                 125

<210> SEQ ID NO 8
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 8

Asp Ile Val Met Thr Gln Ser His Lys Phe Met Ser Thr Ser Leu Gly
1               5                   10                  15
```

Asp Arg Val Asn Ile Thr Cys Lys Ala Ser Leu Ala Val Gly Thr Ala
            20                  25                  30

Val Ala Trp Tyr Gln Lys Pro Gly Gln Ser Pro Lys Leu Leu Ile
        35                  40                  45

Tyr Trp Ala Ser Thr Arg Pro Thr Gly Val Pro Ser Arg Phe Thr Gly
 50                  55                  60

Ser Gly Ser Gly Thr Asp Phe Thr Leu Thr Ile Ser Asn Val Gln Ser
65                  70                  75                  80

Glu Asp Leu Thr Asp Phe Phe Cys Gln Gln Tyr Ser Ser Tyr Pro Leu
                85                  90                  95

Thr Phe Gly Ala Gly Thr Lys Leu Glu Leu Lys
            100                 105

<210> SEQ ID NO 9
<211> LENGTH: 142
<212> TYPE: PRT
<213> ORGANISM: Artificial Sequence
<220> FEATURE:
<223> OTHER INFORMATION: Synthetic Polypeptide

<400> SEQUENCE: 9

Met Leu Glu Trp Ser Trp Val Ile Leu Phe Leu Leu Ser Gly Thr Ala
1               5                   10                  15

Gly Val His Ser Glu Val Gln Leu Gln Gln Ser Gly Pro Glu Leu Val
            20                  25                  30

Lys Pro Gly Ala Ser Met Lys Ile Ser Cys Lys Ala Ser Gly Tyr Ser
        35                  40                  45

Phe Thr Gly Tyr Thr Leu Thr Trp Val Lys Gln Ser His Gly Lys Asn
 50                  55                  60

Leu Asp Trp Ile Gly Leu Ile Asn Pro Tyr Asn Gly Gly Thr Arg Tyr
65                  70                  75                  80

Asn Gln Lys Phe Lys Gly Lys Ala Thr Leu Thr Val Asp Lys Ser Ser
                85                  90                  95

Ser Thr Ala Tyr Met Glu Leu Leu Ser Leu Thr Ser Glu Asp Ser Ala
            100                 105                 110

Val Tyr Tyr Cys Ala Arg Leu Gly Tyr Tyr Ala Thr Gly Asp Glu Tyr
        115                 120                 125

Phe Asp Tyr Trp Gly Gln Gly Thr Thr Leu Thr Val Ser Ser
130                 135                 140

<210> SEQ ID NO 10
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 10

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Leu Thr Trp Val Lys Gln Ser His Gly Lys Asn Leu Asp Trp Ile
        35                  40                  45

Gly Leu Ile Asn Pro Tyr Asn Gly Gly Thr Arg Tyr Asn Gln Lys Phe
 50                  55                  60

Lys Gly Lys Ala Thr Leu Thr Val Asp Lys Ser Ser Ser Thr Ala Tyr

```
                65                  70                  75                  80
Met Glu Leu Leu Ser Leu Thr Ser Asp Ser Ala Val Tyr Tyr Cys
                    85                  90                  95

Ala Arg Leu Gly Tyr Tyr Ala Thr Gly Asp Glu Tyr Phe Asp Tyr Trp
                100                 105                 110

Gly Gln Gly Thr Thr Leu Thr Val Ser Ser
            115                 120

<210> SEQ ID NO 11
<211> LENGTH: 127
<212> TYPE: PRT
<213> ORGANISM: Artificial Sequence
<220> FEATURE:
<223> OTHER INFORMATION: Synthetic Polypeptide

<400> SEQUENCE: 11

Met Lys Ser His Thr Gln Val Phe Ile Tyr Met Leu Leu Trp Leu Ser
1               5                   10                  15

Gly Val Glu Gly Asp Ile Val Met Thr Gln Ser His Lys Phe Met Ser
                20                  25                  30

Thr Ser Val Gly Asp Arg Val Ser Ile Thr Cys Lys Ala Ser Gln Asp
            35                  40                  45

Val Gly Thr Ala Val Ala Trp Tyr Gln Gln Lys Pro Gly Gln Ser Pro
        50                  55                  60

Lys Leu Leu Ile Tyr Trp Ala Ser Thr Arg His Thr Gly Val Pro Asp
65                  70                  75                  80

Arg Phe Thr Gly Ser Arg Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
                100                 105                 110

Ser Tyr Pro Cys Thr Phe Gly Gly Gly Ala Lys Leu Glu Ile Arg
            115                 120                 125

<210> SEQ ID NO 12
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 12

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Arg Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Cys
                85                  90                  95

Thr Phe Gly Gly Gly Ala Lys Leu Glu Ile Arg
            100                 105

<210> SEQ ID NO 13
<211> LENGTH: 119
```

```
<212> TYPE: PRT
<213> ORGANISM: Artificial Sequence
<220> FEATURE:
<223> OTHER INFORMATION: Synthetic Polypeptide

<400> SEQUENCE: 13

Glu Val Gln Leu Gln Gln Ser Gly Thr Val Leu Ala Arg Pro Gly Ala
1               5                   10                  15

Ser Val Lys Met Ser Cys Lys Ala Ser Ala Tyr Thr Phe Thr Arg Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Thr Tyr Asn Gln Lys Phe
50                  55                  60

Lys Gly Lys Ala Lys Leu Thr Ala Val Thr Ser Thr Ser Thr Ala Tyr
65                  70                  75                  80

Met Glu Leu Ser Ser Leu Thr Asn Glu Asp Ser Ala Val Tyr Tyr Cys
                85                  90                  95

Thr Lys Lys Gly Val Arg Tyr Tyr Ala Leu Asp Tyr Trp Gly Gln Gly
                100                 105                 110

Thr Ser Val Thr Val Ser Ser
            115

<210> SEQ ID NO 14
<211> LENGTH: 132
<212> TYPE: PRT
<213> ORGANISM: Artificial Sequence
<220> FEATURE:
<223> OTHER INFORMATION: Synthetic Polypeptide

<400> SEQUENCE: 14

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Tyr Gly Asn Ser Phe Val His Trp Tyr Gln Gln Lys Pro
50                  55                  60

Gly Gln Pro Pro Lys Leu Leu Ile Tyr Arg Ala Ser Asn Leu Glu Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Thr Tyr Tyr Cys
                100                 105                 110

Leu Gln Ser Asn Glu Asp Pro Met Tyr Thr Phe Gly Gly Gly Thr Lys
                115                 120                 125

Leu Glu Ile Lys
    130

<210> SEQ ID NO 15
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 15

Asp Ile Val Leu Thr Gln Ser Pro Ala Ser Leu Ala Val Ser Leu Gly
```

```
1               5                   10                  15
Gln Arg Ala Thr Ile Ser Cys Arg Ala Ser Glu Ser Val Asp Ser Tyr
            20                  25                  30

Gly Asn Ser Phe Val His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
            50                  55                  60

Arg Phe Ser Gly Ser Gly Ser Arg Thr Asp Phe Thr Leu Thr Ile Asn
 65                 70                  75                  80

Pro Val Glu Ala Asp Asp Val Ala Thr Tyr Tyr Cys Leu Gln Ser Asn
                85                  90                  95

Glu Asp Pro Met Tyr Thr Phe Gly Gly Gly Thr Lys Leu Glu Ile Lys
            100                 105                 110

<210> SEQ ID NO 16
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 16

Met Asp Phe Gly Leu Ser Leu Val Phe Leu Val Leu Ile Leu Lys Gly
 1               5                  10                  15

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
            35                  40                  45

Thr Gly Tyr Thr Leu Thr Trp Val Lys Gln Ser His Gly Lys Asn Leu
            50                  55                  60

Asp Trp Ile Gly Leu Ile Asn Pro Tyr Ser Gly Gly Thr Arg Tyr Asn
 65                 70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Leu Gly Tyr Tyr Ala Thr Gly Asp Glu Tyr Phe
            115                 120                 125

Asp Tyr Trp Gly Gln Gly Thr Thr Leu Thr Val Ser Ser
            130                 135                 140

<210> SEQ ID NO 17
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 17

Glu Val Gln Leu Gln Gln Ser Gly Pro Glu Leu Val Lys Pro Gly Ala
 1               5                  10                  15

Ser Met Lys Ile Ser Cys Lys Ala Ser Gly Tyr Ser Phe Thr Gly Tyr
            20                  25                  30

Thr Leu Thr Trp Val Lys Gln Ser His Gly Lys Asn Leu Asp Trp Ile
            35                  40                  45

Gly Leu Ile Asn Pro Tyr Ser Gly Gly Thr Arg Tyr Asn Gln Lys Phe
            50                  55                  60
```

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Leu Gly Tyr Tyr Ala Thr Gly Asp Glu Tyr Phe Asp Tyr Trp
            100                 105                 110

Gly Gln Gly Thr Thr Leu Thr Val Ser Ser
        115                 120

<210> SEQ ID NO 18
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 18

Met Asp Phe Gly Leu Ser Leu Val Phe Leu Val Leu Ile Leu Lys Gly
1               5                   10                  15

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Leu Thr Trp Val Lys Gln Ser His Gly Lys Asn Leu
    50                  55                  60

Asp Trp Ile Gly Leu Ile Asn Pro Tyr Gln Gly Gly Thr Arg Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Leu Gly Tyr Tyr Ala Thr Gly Asp Glu Tyr Phe
        115                 120                 125

Asp Tyr Trp Gly Gln Gly Thr Thr Leu Thr Val Ser Ser
    130                 135                 140

<210> SEQ ID NO 19
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 19

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Leu Thr Trp Val Lys Gln Ser His Gly Lys Asn Leu Asp Trp Ile
        35                  40                  45

Gly Leu Ile Asn Pro Tyr Gln Gly Gly Thr Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Leu Gly Tyr Tyr Ala Thr Gly Asp Glu Tyr Phe Asp Tyr Trp
            100                 105                 110

Gly Gln Gly Thr Thr Leu Thr Val Ser Ser
        115                 120

<210> SEQ ID NO 20
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 20

Met Asp Phe Gly Leu Ser Leu Val Phe Leu Val Leu Ile Leu Lys Gly
1               5                   10                  15

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Leu Thr Trp Val Lys Gln Ser His Gly Lys Asn Leu
    50                  55                  60

Asp Trp Ile Gly Leu Ile Asn Pro Tyr Asp Gly Thr Arg Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Leu Gly Tyr Tyr Ala Thr Gly Asp Glu Tyr Phe
        115                 120                 125

Asp Tyr Trp Gly Gln Gly Thr Thr Leu Thr Val Ser Ser
    130                 135                 140

<210> SEQ ID NO 21
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 21

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Leu Thr Trp Val Lys Gln Ser His Gly Lys Asn Leu Asp Trp Ile
        35                  40                  45

Gly Leu Ile Asn Pro Tyr Asp Gly Thr Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Leu Gly Tyr Tyr Ala Thr Gly Asp Glu Tyr Phe Asp Tyr Trp
            100                 105                 110

Gly Gln Gly Thr Thr Leu Thr Val Ser Ser
        115                 120

<210> SEQ ID NO 22
<211> LENGTH: 141
<212> TYPE: PRT

<213> ORGANISM: Artificial Sequence
<220> FEATURE:
<223> OTHER INFORMATION: Synthetic Polypeptide

<400> SEQUENCE: 22

```
Met Asp Phe Gly Leu Ser Leu Val Phe Leu Val Leu Ile Leu Lys Gly
1               5                   10                  15

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Leu Thr Trp Val Lys Gln Ser His Gly Lys Asn Leu
    50                  55                  60

Asp Trp Ile Gly Leu Ile Asn Pro Tyr His Gly Gly Thr Arg Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Leu Gly Tyr Tyr Ala Thr Gly Asp Glu Tyr Phe
        115                 120                 125

Asp Tyr Trp Gly Gln Gly Thr Thr Leu Thr Val Ser Ser
    130                 135                 140
```

<210> SEQ ID NO 23
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 23

```
Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Leu Thr Trp Val Lys Gln Ser His Gly Lys Asn Leu Asp Trp Ile
        35                  40                  45

Gly Leu Ile Asn Pro Tyr His Gly Gly Thr Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Leu Gly Tyr Tyr Ala Thr Gly Asp Glu Tyr Phe Asp Tyr Trp
            100                 105                 110

Gly Gln Gly Thr Thr Leu Thr Val Ser Ser
        115                 120
```

<210> SEQ ID NO 24
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 24

```
Met Asp Phe Gly Leu Ser Leu Val Phe Leu Val Leu Ile Leu Lys Gly
1               5                   10                  15
```

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Leu Thr Trp Val Lys Gln Ser His Gly Lys Asn Leu
    50                  55                  60

Asp Trp Ile Gly Leu Ile Asn Pro Tyr Thr Gly Thr Arg Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Leu Gly Tyr Tyr Ala Thr Gly Asp Glu Tyr Phe
        115                 120                 125

Asp Tyr Trp Gly Gln Gly Thr Thr Leu Thr Val Ser Ser
    130                 135                 140

<210> SEQ ID NO 25
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 25

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Leu Thr Trp Val Lys Gln Ser His Gly Lys Asn Leu Asp Trp Ile
        35                  40                  45

Gly Leu Ile Asn Pro Tyr Thr Gly Thr Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Leu Gly Tyr Tyr Ala Thr Gly Asp Glu Tyr Phe Asp Tyr Trp
            100                 105                 110

Gly Gln Gly Thr Thr Leu Thr Val Ser Ser
        115                 120

<210> SEQ ID NO 26
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 26

Met Asp Phe Gly Leu Ser Leu Val Phe Leu Val Leu Ile Leu Lys Gly
1               5                   10                  15

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Leu Thr Trp Val Lys Gln Ser His Gly Lys Asn Leu

```
            50                  55                  60
Asp Trp Ile Gly Leu Ile Asn Pro Tyr Ala Gly Gly Thr Arg Tyr Asn
 65                  70                  75                  80

Gln Lys Phe Lys Gly Lys Ala Thr Leu Thr Val Asp Lys Ser Ser Ser
                 85                  90                  95

Thr Ala Tyr Met Glu Leu Leu Ser Leu Thr Ser Glu Asp Ser Ala Val
            100                 105                 110

Tyr Tyr Cys Ala Arg Leu Gly Tyr Tyr Ala Thr Gly Asp Glu Tyr Phe
        115                 120                 125

Asp Tyr Trp Gly Gln Gly Thr Thr Leu Thr Val Ser Ser
    130                 135                 140
```

<210> SEQ ID NO 27
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 27

```
Glu Val Gln Leu Gln Gln Ser Gly Pro Glu Leu Val Lys Pro Gly Ala
 1               5                  10                  15

Ser Met Lys Ile Ser Cys Lys Ala Ser Gly Tyr Ser Phe Thr Gly Tyr
                 20                  25                  30

Thr Leu Thr Trp Val Lys Gln Ser His Gly Lys Asn Leu Asp Trp Ile
             35                  40                  45

Gly Leu Ile Asn Pro Tyr Ala Gly Gly Thr Arg Tyr Asn Gln Lys Phe
         50                  55                  60

Lys Gly Lys Ala Thr Leu Thr Val Asp Lys Ser Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Leu Gly Tyr Tyr Ala Thr Gly Asp Glu Tyr Phe Asp Tyr Trp
            100                 105                 110

Gly Gln Gly Thr Thr Leu Thr Val Ser Ser
        115                 120
```

<210> SEQ ID NO 28
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 28

```
Met Asp Phe Gly Leu Ser Leu Val Phe Leu Val Leu Ile Leu Lys Gly
 1               5                  10                  15

Val Gln Cys Glu Val Gln Leu Gln Gln Ser Gly Pro Glu Leu Val Lys
                 20                  25                  30

Pro Gly Ala Ser Met Lys Ile Ser Cys Lys Ala Ser Gly Tyr Ser Phe
             35                  40                  45

Thr Gly Tyr Thr Leu Thr Trp Val Lys Gln Ser His Gly Lys Asn Leu
         50                  55                  60

Asp Trp Ile Gly Leu Ile Asn Pro Tyr Leu Gly Gly Thr Arg Tyr Asn
 65                  70                  75                  80

Gln Lys Phe Lys Gly Lys Ala Thr Leu Thr Val Asp Lys Ser Ser Ser
                 85                  90                  95
```

```
Thr Ala Tyr Met Glu Leu Leu Ser Leu Thr Ser Glu Asp Ser Ala Val
            100                 105                 110

Tyr Tyr Cys Ala Arg Leu Gly Tyr Tyr Ala Thr Gly Asp Glu Tyr Phe
        115                 120                 125

Asp Tyr Trp Gly Gln Gly Thr Thr Leu Thr Val Ser Ser
    130                 135                 140

<210> SEQ ID NO 29
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 29

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Leu Thr Trp Val Lys Gln Ser His Gly Lys Asn Leu Asp Trp Ile
        35                  40                  45

Gly Leu Ile Asn Pro Tyr Leu Gly Gly Thr Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Leu Gly Tyr Tyr Ala Thr Gly Asp Glu Tyr Phe Asp Tyr Trp
            100                 105                 110

Gly Gln Gly Thr Thr Leu Thr Val Ser Ser
        115                 120

<210> SEQ ID NO 30
<211> LENGTH: 141
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (74)..(74)
<223> OTHER INFORMATION: Xaa can be any naturally occurring amino acid

<400> SEQUENCE: 30

Met Asp Phe Gly Leu Ser Leu Val Phe Leu Val Leu Ile Leu Lys Gly
1               5                   10                  15

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Leu Thr Trp Val Lys Gln Ser His Gly Lys Asn Leu
    50                  55                  60

Asp Trp Ile Gly Leu Ile Asn Pro Tyr Xaa Gly Gly Thr Arg Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Leu Gly Tyr Tyr Ala Thr Gly Asp Glu Tyr Phe
```

Asp Tyr Trp Gly Gln Gly Thr Thr Leu Thr Val Ser Ser
            130                 135                 140

<210> SEQ ID NO 31
<211> LENGTH: 122
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (55)..(55)
<223> OTHER INFORMATION: Xaa can be any naturally occurring amino acid

<400> SEQUENCE: 31

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Leu Thr Trp Val Lys Gln Ser His Gly Lys Asn Leu Asp Trp Ile
        35                  40                  45

Gly Leu Ile Asn Pro Tyr Xaa Gly Gly Thr Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Leu Gly Tyr Tyr Ala Thr Gly Asp Glu Tyr Phe Asp Tyr Trp
            100                 105                 110

Gly Gln Gly Thr Thr Leu Thr Val Ser Ser
        115                 120

<210> SEQ ID NO 32
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 32

Met Asp Phe Gly Leu Ser Leu Val Phe Leu Val Leu Ile Leu Lys Gly
1               5                   10                  15

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Leu Thr Trp Val Lys Gln Ser His Gly Lys Asn Leu
    50                  55                  60

Asp Trp Ile Gly Leu Ile Asn Pro Tyr Asn Ala Gly Thr Arg Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Leu Gly Tyr Tyr Ala Thr Gly Asp Glu Tyr Phe
        115                 120                 125

Asp Tyr Trp Gly Gln Gly Thr Thr Leu Thr Val Ser Ser
    130                 135                 140

<210> SEQ ID NO 33
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 33

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Leu Thr Trp Val Lys Gln Ser His Gly Lys Asn Leu Asp Trp Ile
        35                  40                  45

Gly Leu Ile Asn Pro Tyr Asn Ala Gly Thr Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Leu Gly Tyr Tyr Ala Thr Gly Asp Glu Tyr Phe Asp Tyr Trp
            100                 105                 110

Gly Gln Gly Thr Thr Leu Thr Val Ser Ser
        115                 120

<210> SEQ ID NO 34
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 34

Met Asp Phe Gly Leu Ser Leu Val Phe Leu Val Leu Ile Leu Lys Gly
1               5                   10                  15

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Leu Thr Trp Val Lys Gln Ser His Gly Lys Asn Leu
    50                  55                  60

Asp Trp Ile Gly Leu Ile Asn Pro Tyr Asn Val Gly Thr Arg Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Leu Gly Tyr Tyr Ala Thr Gly Asp Glu Tyr Phe
        115                 120                 125

Asp Tyr Trp Gly Gln Gly Thr Thr Leu Thr Val Ser Ser
    130                 135                 140

<210> SEQ ID NO 35
<211> LENGTH: 122
<212> TYPE: PRT
<213> ORGANISM: Artificial Sequence
<220> FEATURE:
<223> OTHER INFORMATION: Synthetic Polypeptide

```
<400> SEQUENCE: 35

Glu Val Gln Leu Gln Gln Ser Gly Pro Glu Leu Val Lys Pro Gly Ala
1               5                  10                  15

Ser Met Lys Ile Ser Cys Lys Ala Ser Gly Tyr Ser Phe Thr Gly Tyr
            20                  25                  30

Thr Leu Thr Trp Val Lys Gln Ser His Gly Lys Asn Leu Asp Trp Ile
        35                  40                  45

Gly Leu Ile Asn Pro Tyr Asn Val Gly Thr Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Leu Gly Tyr Tyr Ala Thr Gly Asp Glu Tyr Phe Asp Tyr Trp
            100                 105                 110

Gly Gln Gly Thr Thr Leu Thr Val Ser Ser
        115                 120

<210> SEQ ID NO 36
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 36

Met Asp Phe Gly Leu Ser Leu Val Phe Leu Val Leu Ile Leu Lys Gly
1               5                  10                  15

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Leu Thr Trp Val Lys Gln Ser His Gly Lys Asn Leu
    50                  55                  60

Asp Trp Ile Gly Leu Ile Asn Pro Tyr Asn Pro Gly Thr Arg Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Leu Gly Tyr Tyr Ala Thr Gly Asp Glu Tyr Phe
        115                 120                 125

Asp Tyr Trp Gly Gln Gly Thr Thr Leu Thr Val Ser Ser
    130                 135                 140

<210> SEQ ID NO 37
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 37

Glu Val Gln Leu Gln Gln Ser Gly Pro Glu Leu Val Lys Pro Gly Ala
1               5                  10                  15

Ser Met Lys Ile Ser Cys Lys Ala Ser Gly Tyr Ser Phe Thr Gly Tyr
            20                  25                  30
```

```
Thr Leu Thr Trp Val Lys Gln Ser His Gly Lys Asn Leu Asp Trp Ile
         35                  40                  45

Gly Leu Ile Asn Pro Tyr Asn Pro Gly Thr Arg Tyr Asn Gln Lys Phe
     50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                 85                  90                  95

Ala Arg Leu Gly Tyr Tyr Ala Thr Gly Asp Glu Tyr Phe Asp Tyr Trp
            100                 105                 110

Gly Gln Gly Thr Thr Leu Thr Val Ser Ser
            115                 120

<210> SEQ ID NO 38
<211> LENGTH: 141
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (75)..(75)
<223> OTHER INFORMATION: Xaa can be any naturally occurring amino acid

<400> SEQUENCE: 38

Met Asp Phe Gly Leu Ser Leu Val Phe Leu Val Leu Ile Leu Lys Gly
1               5                   10                  15

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
         35                  40                  45

Thr Gly Tyr Thr Leu Thr Trp Val Lys Gln Ser His Gly Lys Asn Leu
     50                  55                  60

Asp Trp Ile Gly Leu Ile Asn Pro Tyr Asn Xaa Gly Thr Arg Tyr Asn
65                  70                  75                  80

Gln Lys Phe Lys Gly Lys Ala Thr Leu Thr Val Asp Lys Ser Ser Ser
                 85                  90                  95

Thr Ala Tyr Met Glu Leu Leu Ser Leu Thr Ser Glu Asp Ser Ala Val
            100                 105                 110

Tyr Tyr Cys Ala Arg Leu Gly Tyr Tyr Ala Thr Gly Asp Glu Tyr Phe
         115                 120                 125

Asp Tyr Trp Gly Gln Gly Thr Thr Leu Thr Val Ser Ser
     130                 135                 140

<210> SEQ ID NO 39
<211> LENGTH: 122
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (56)..(56)
<223> OTHER INFORMATION: Xaa can be any naturally occurring amino acid

<400> SEQUENCE: 39

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30
```

```
Thr Leu Thr Trp Val Lys Gln Ser His Gly Lys Asn Leu Asp Trp Ile
            35                  40                  45

Gly Leu Ile Asn Pro Tyr Asn Xaa Gly Thr Arg Tyr Asn Gln Lys Phe
        50                  55                  60

Lys Gly Lys Ala Thr Leu Thr Val Asp Lys Ser Ser Thr Ala Tyr
 65                  70                  75                  80

Met Glu Leu Leu Ser Leu Thr Ser Glu Asp Ser Ala Val Tyr Tyr Cys
                85                  90                  95

Ala Arg Leu Gly Tyr Tyr Ala Thr Gly Asp Glu Tyr Phe Asp Tyr Trp
                100                 105                 110

Gly Gln Gly Thr Thr Leu Thr Val Ser Ser
            115                 120

<210> SEQ ID NO 40
<211> LENGTH: 127
<212> TYPE: PRT
<213> ORGANISM: Artificial Sequence
<220> FEATURE:
<223> OTHER INFORMATION: Synthetic Polypeptide

<400> SEQUENCE: 40

Met Arg Val Pro Ala Gln Leu Leu Gly Leu Leu Leu Leu Trp Leu Pro
 1               5                  10                  15

Gly Ala Arg Cys Asp Ile Val Met Thr Gln Ser His Lys Phe Met Ser
                20                  25                  30

Thr Ser Val Gly Asp Arg Val Ser Ile Thr Cys Lys Ala Ser Gln Asp
            35                  40                  45

Val Gly Thr Ala Val Ala Trp Tyr Gln Gln Lys Pro Gly Gln Ser Pro
        50                  55                  60

Lys Leu Leu Ile Tyr Trp Ala Ser Thr Arg His Thr Gly Val Pro Asp
 65                  70                  75                  80

Arg Phe Thr Gly Ser Arg Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
                100                 105                 110

Ser Tyr Pro Leu Thr Phe Gly Gly Gly Ala Lys Leu Glu Ile Arg
            115                 120                 125

<210> SEQ ID NO 41
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 41

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Arg Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr Pro Leu
```

```
                85                  90                  95
Thr Phe Gly Gly Gly Ala Lys Leu Glu Ile Arg
            100                 105

<210> SEQ ID NO 42
<211> LENGTH: 127
<212> TYPE: PRT
<213> ORGANISM: Artificial Sequence
<220> FEATURE:
<223> OTHER INFORMATION: Synthetic Polypeptide

<400> SEQUENCE: 42

Met Arg Val Pro Ala Gln Leu Leu Gly Leu Leu Leu Leu Trp Leu Pro
1               5                   10                  15

Gly Ala Arg Cys Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Gly Thr Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Arg Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Tyr Pro Ser Thr Phe Gly Gly Gly Ala Lys Leu Glu Ile Arg
        115                 120                 125

<210> SEQ ID NO 43
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 43

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Arg Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Ser
                85                  90                  95

Thr Phe Gly Gly Gly Ala Lys Leu Glu Ile Arg
            100                 105

<210> SEQ ID NO 44
<211> LENGTH: 127
<212> TYPE: PRT
<213> ORGANISM: Artificial Sequence
<220> FEATURE:
<223> OTHER INFORMATION: Synthetic Polypeptide

<400> SEQUENCE: 44
```

Met Arg Val Pro Ala Gln Leu Leu Gly Leu Leu Leu Trp Leu Pro
1               5                   10                  15

Gly Ala Arg Cys Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Gly Thr Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65              70                  75                  80

Arg Phe Thr Gly Ser Arg Ser Gly Thr Asp Phe Thr Leu Thr Ile Ser
            85                  90                  95

Asn Val Gln Ser Glu Asp Leu Ala Asp Tyr Phe Cys Gln Gln Tyr Ser
        100                 105                 110

Ser Tyr Pro Ala Thr Phe Gly Gly Gly Ala Lys Leu Glu Ile Arg
            115                 120                 125

<210> SEQ ID NO 45
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 45

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Arg Ser Gly Thr Asp Phe Thr Leu Thr Ile Ser Asn Val Gln Ser
65              70                  75                  80

Glu Asp Leu Ala Asp Tyr Phe Cys Gln Gln Tyr Ser Ser Tyr Pro Ala
            85                  90                  95

Thr Phe Gly Gly Gly Ala Lys Leu Glu Ile Arg
            100                 105

<210> SEQ ID NO 46
<211> LENGTH: 127
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (116)..(116)
<223> OTHER INFORMATION: Xaa can be any naturally occurring amino acid

<400> SEQUENCE: 46

Met Arg Val Pro Ala Gln Leu Leu Gly Leu Leu Leu Trp Leu Pro
1               5                   10                  15

Gly Ala Arg Cys Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

```
Val Gly Thr Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
 65                  70                  75                  80

Arg Phe Thr Gly Ser Arg Ser Gly Thr Asp Phe Thr Leu Thr Ile Ser
                 85                  90                  95

Asn Val Gln Ser Glu Asp Leu Ala Asp Tyr Phe Cys Gln Gln Tyr Ser
            100                 105                 110

Ser Tyr Pro Xaa Thr Phe Gly Gly Gly Ala Lys Leu Glu Ile Arg
        115                 120                 125
```

<210> SEQ ID NO 47
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (96)..(96)
<223> OTHER INFORMATION: Xaa can be any naturally occurring amino acid

<400> SEQUENCE: 47

```
Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
 50                  55                  60

Ser Arg Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr Pro Xaa
                 85                  90                  95

Thr Phe Gly Gly Gly Ala Lys Leu Glu Ile Arg
            100                 105
```

<210> SEQ ID NO 48
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 48

```
Gly Tyr Thr Leu Thr
 1               5
```

<210> SEQ ID NO 49
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 49

```
Leu Ile Asn Pro Tyr Asn Gly Gly Thr Arg Tyr Asn Gln Lys Phe Lys
 1               5                  10                  15

Gly
```

```
<210> SEQ ID NO 50
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 50

Leu Ile Asn Pro Tyr Ser Gly Gly Thr Arg Tyr Asn Gln Lys Phe Lys
1               5                   10                  15

Gly

<210> SEQ ID NO 51
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 51

Leu Ile Asn Pro Tyr Gln Gly Gly Thr Arg Tyr Asn Gln Lys Phe Lys
1               5                   10                  15

Gly

<210> SEQ ID NO 52
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 52

Leu Ile Asn Pro Tyr Asp Gly Gly Thr Arg Tyr Asn Gln Lys Phe Lys
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 53

Leu Ile Asn Pro Tyr His Gly Gly Thr Arg Tyr Asn Gln Lys Phe Lys
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 54

Leu Ile Asn Pro Tyr Thr Gly Gly Thr Arg Tyr Asn Gln Lys Phe Lys
1               5                   10                  15

Gly

<210> SEQ ID NO 55
<211> LENGTH: 17
<212> TYPE: PRT
<213> ORGANISM: Artificial Sequence
```

<220> FEATURE:
<223> OTHER INFORMATION: Synthetic Polypeptide

<400> SEQUENCE: 55

Leu Ile Asn Pro Tyr Ala Gly Gly Thr Arg Tyr Asn Gln Lys Phe Lys
1               5                   10                  15
Gly

<210> SEQ ID NO 56
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 56

Leu Ile Asn Pro Tyr Leu Gly Gly Thr Arg Tyr Asn Gln Lys Phe Lys
1               5                   10                  15
Gly

<210> SEQ ID NO 57
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 57

Leu Ile Asn Pro Tyr Xaa Gly Gly Thr Arg Tyr Asn Gln Lys Phe Lys
1               5                   10                  15
Gly

<210> SEQ ID NO 58
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 58

Leu Ile Asn Pro Tyr Asn Ala Gly Thr Arg Tyr Asn Gln Lys Phe Lys
1               5                   10                  15
Gly

<210> SEQ ID NO 59
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 59

Leu Ile Asn Pro Tyr Asn Val Gly Thr Arg Tyr Asn Gln Lys Phe Lys
1               5                   10                  15
Gly

<210> SEQ ID NO 60
<211> LENGTH: 17
<212> TYPE: PRT
<213> ORGANISM: Artificial Sequence

```
<220> FEATURE:
<223> OTHER INFORMATION: Synthetic Polypeptide

<400> SEQUENCE: 60

Leu Ile Asn Pro Tyr Asn Pro Gly Thr Arg Tyr Asn Gln Lys Phe Lys
1               5                   10                  15

Gly

<210> SEQ ID NO 61
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 61

Leu Ile Asn Pro Tyr Asn Xaa Gly Thr Arg Tyr Asn Gln Lys Phe Lys
1               5                   10                  15

Gly

<210> SEQ ID NO 62
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(7)
<223> OTHER INFORMATION: Xaa can be any naturally occurring amino acid

<400> SEQUENCE: 62

Leu Ile Asn Pro Tyr Xaa Xaa Gly Thr Arg Tyr Asn Gln Lys Phe Lys
1               5                   10                  15

Gly

<210> SEQ ID NO 63
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 63

Leu Gly Tyr Tyr Ala Thr Gly Asp Glu Tyr Phe Asp Tyr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 64

Lys Ala Ser Gln Asp Val Gly Thr Ala Val Ala
1               5                   10

<210> SEQ ID NO 65
<211> LENGTH: 7
<212> TYPE: PRT
<213> ORGANISM: Artificial Sequence
```

```
<220> FEATURE:
<223> OTHER INFORMATION: Synthetic Polypeptide

<400> SEQUENCE: 65

Trp Ala Ser Thr Arg His Thr
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 66

Gln Gln Tyr Ser Ser Tyr Pro Cys Thr
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 67

Gln Gln Tyr Ser Ser Tyr Pro Leu Thr
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 68

Gln Gln Tyr Ser Ser Tyr Pro Ser Thr
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 69

Gln Gln Tyr Ser Ser Tyr Pro Ala Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 70

Gln Gln Tyr Ser Ser Tyr Pro Xaa Thr
1               5

<210> SEQ ID NO 71
```

<211> LENGTH: 470
<212> TYPE: PRT
<213> ORGANISM: Artificial Sequence
<220> FEATURE:
<223> OTHER INFORMATION: Synthetic Polypeptide

<400> SEQUENCE: 71

```
Met Asp Phe Gly Leu Ser Leu Val Phe Leu Val Leu Ile Leu Lys Gly
1               5                   10                  15

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Leu Thr Trp Val Lys Gln Ser His Gly Lys Asn Leu
    50                  55                  60

Asp Trp Ile Gly Leu Ile Asn Pro Tyr His Gly Thr Arg Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Leu Gly Tyr Ala Thr Gly Asp Glu Tyr Phe
        115                 120                 125

Asp Tyr Trp Gly Gln Gly Thr Thr Leu Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380
```

```
Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly
465                 470

<210> SEQ ID NO 72
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 72

Met Arg Val Pro Ala Gln Leu Leu Gly Leu Leu Leu Leu Trp Leu Pro
1               5                   10                  15

Gly Ala Arg Cys Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Gly Thr Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Arg Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Tyr Pro Ser Thr Phe Gly Gly Gly Ala Lys Leu Glu Ile Arg Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 73
<211> LENGTH: 1410
<212> TYPE: DNA
<213> ORGANISM: Artificial Sequence
```

<220> FEATURE:
<223> OTHER INFORMATION: Synthetic Polynucleotide

<400> SEQUENCE: 73

```
atggacttcg ggttgagctt ggttttcctt gtcctaattt taaaaggtgt ccagtgtgaa      60
gtgcagctgc agcagtccgg ccctgagctg gtgaaacctg gcgcctccat gaagatcagc     120
tgcaaggcct ccggctactc cttcaccggc tacaccctga cctgggtgaa acagtcccac     180
ggcaagaacc tggactggat cggcctgatc aaccccacc acggcggcac ccggtacaac     240
cagaagttca agggcaaggc caccctgacc gtggacaagt cctcctccac cgcctacatg     300
gaactgctgt ccctgacctc cgaggactcc gccgtgtact actgcgccag actgggctac     360
tacgccaccg cgacgagta cttcgactac tggggccagg gcaccaccct gacagtgtcc     420
tccgcctcta ccaagggccc ctccgtgttc cctctggccc cctccagcaa gtccacctct     480
ggcggcaccg ccgctctggg ctgcctggtc aaggactact ccccgaaccc ggtgacggtg     540
tcgtggaact caggcgccct gaccagcggc gtgcacacct tcccggctgt cctacagtcc     600
tcaggactct actccctcag cagcgtggtg accgtgccct ccagcagctt gggcacccag     660
acctacatct gcaacgtgaa tcacaagccc agcaacacca aggtggacaa gaaagttgag     720
cccaaatctt gtgacaagac tcacacatgc ccaccgtgcc cagcacctga actcctgggg     780
ggaccgtcag tcttcctctt ccccccaaaa cccaaggaca cctcatgat ctcccggacc      840
cctgaggtca catgcgtggt ggtggacgtg agccacgaag accctgaggt caagttcaac     900
tggtacgtgg acggcgtgga ggtgcataat gccaagacaa agccgcggga ggagcagtac     960
aacagcacgt accgtgtggt cagcgtcctc accgtcctgc accaggactg gctgaatggc    1020
aaggagtaca agtgcaaggt ctccaacaaa gccctcccag cccccatcga gaaaaccatc    1080
tccaaagcca agggcagcc ccgagaacca caggtgtaca cctgcccccc atcccgggat     1140
gagctgacca gaaccaggt cagcctgacc tgcctggtca aaggcttcta tcccagcgac    1200
atcgccgtgg agtgggagag caatgggcag ccggagaaca actacaagac cacgcctccc    1260
gtgttggact ccgacggctc cttcttcctc tacagcaagc tcaccgtgga caagagcagg    1320
tggcagcagg ggaacgtctt ctcatgctcc gtgatgcatg aggctctgca caaccactac    1380
acgcagaaga gcctctccct gtctcccggt                                    1410
```

<210> SEQ ID NO 74
<211> LENGTH: 702
<212> TYPE: DNA
<213> ORGANISM: Artificial Sequence
<220> FEATURE:
<223> OTHER INFORMATION: Synthetic Polynucleotide

<400> SEQUENCE: 74

```
atgagggtcc ccgctcagct cctggggctc cttctgctct ggctccctgg agccagatgt      60
gacatcgtga tgacccagtc ccacaagttc atgtccacct ccgtgggcga ccgggtgtcc     120
atcacatgca aggcctccca ggacgtgggc accgccgtgg cctggtatca gcagaagccc     180
ggccagtccc ccaagctgct gatctactgg gcctccacca gacacaccgg cgtgcccgac     240
agattcaccg gctccagatc cggcaccgac ttcaccctga ccatctccaa cgtgcagtcc     300
gaggacctgg ccgactactt ctgccagcag tactcctcct accccagcac cttcggcgga     360
ggcgccaagc tggaaatccg cgtacggtg gctgcaccat ctgtcttcat cttcccgcca     420
tctgatgagc agttgaaatc tggaactgcc tctgttgtgt gcctgctgaa taacttctat     480
```

-continued

```
cccagagagg ccaaagtaca gtggaaggtg gataacgccc tccaatcggg taactcccag        540
gagagtgtca cagagcagga cagcaaggac agcacctaca gcctcagcag caccctgacg        600
ctgagcaaag cagactacga gaaacacaaa gtctacgcct gcgaagtcac ccatcagggc        660
ctgagctcgc ccgtcacaaa gagcttcaac aggggagagt gt                          702
```